(12) United States Patent
Diep et al.

(10) Patent No.: US 10,537,286 B2
(45) Date of Patent: Jan. 21, 2020

(54) CATHETER WITH MULTIPLE SPINES OF DIFFERENT LENGTHS ARRANGED IN ONE OR MORE DISTAL ASSEMBLIES

(71) Applicant: Biosense Webster (Israel), Ltd., Yokneam (IL)

(72) Inventors: Nhut Diep, San Francisco, CA (US); Tom Allen Ditter, Chino Hills, CA (US); Raymond Estrada, Fremont, CA (US); Kristine Fuimaono, Covina, CA (US); Debby Grunewald, Los Angeles, CA (US); Ryan Hoitink, Pasadena, CA (US); Eduardo Jimenez, Paramount, CA (US); Armida Manriquez, Eastvale, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 343 days.

(21) Appl. No.: 13/736,794

(22) Filed: Jan. 8, 2013

(65) Prior Publication Data

US 2014/0194716 A1     Jul. 10, 2014

(51) Int. Cl.
*A61B 18/14*     (2006.01)
*A61B 5/00*     (2006.01)
(Continued)

(52) U.S. Cl.
CPC .......... *A61B 5/6859* (2013.01); *A61B 5/0422* (2013.01); *A61B 5/4836* (2013.01);
(Continued)

(58) Field of Classification Search
CPC ...... A61B 2018/1475; A61B 2018/144; A61B 2018/00214; A61B 2018/00351;
(Continued)

(56) References Cited

U.S. PATENT DOCUMENTS

| | | |
|---|---|---|
| 5,391,199 A | 2/1995 | Ben-Haim |
| 5,443,489 A | 8/1995 | Ben-Haim |

(Continued)

FOREIGN PATENT DOCUMENTS

| | | |
|---|---|---|
| AU | 2013201681 B2 | 2/2015 |
| CN | 101797181 B | 12/2015 |

(Continued)

OTHER PUBLICATIONS

EP Communication and European Search Report dated Apr. 28, 2014 for EP Application No. 14150343.3-1659, 9 pgs.
(Continued)

*Primary Examiner* — Jaymi E Della
(74) *Attorney, Agent, or Firm* — Roberts Mlotkowski Safran Cole & Calderon, P.C.

(57) ABSTRACT

A catheter having a distal assembly with multiple spines with proximal ends affixed to the catheter and free distal ends. The spines have different lengths so distal ends of the spines trace different circumferences along an inner tissue surface of a tubular region to minimize risk of vein stenosis. The spine lengths can be configured so that the distal ends trace a helical pattern. The distal assembly may have a plunger which deflects the spines when moved longitudinally relative to the distal assembly. The catheter may include a second distal assembly distal of a first distal assembly wherein the first and second distal assemblies are separated by a fixed distanced or an adjustable distance.

7 Claims, 29 Drawing Sheets

(51) Int. Cl.
*A61B 5/042* (2006.01)
*A61B 18/00* (2006.01)

(52) U.S. Cl.
CPC *A61B 18/1492* (2013.01); *A61B 2018/00386* (2013.01); *A61B 2018/00404* (2013.01)

(58) Field of Classification Search
CPC .. A61B 2018/2018; A61B 2018/00357; A61B 5/6859; A61B 5/0422; A61B 18/1492; A61B 5/4836; A61B 2017/00867; A61B 2017/2018; A61B 2017/0016; A61B 2018/00345; A61B 2018/1435
See application file for complete search history.

(56) References Cited

U.S. PATENT DOCUMENTS

| | | | |
|---|---|---|---|
| 5,480,422 A | 1/1996 | Ben-Haim | |
| 5,546,951 A | 8/1996 | Ben-Haim | |
| 5,558,091 A | 9/1996 | Acker et al. | |
| 5,568,809 A | 10/1996 | Ben-haim | |
| 5,702,438 A | 12/1997 | Avitall | |
| 5,871,523 A | 2/1999 | Fleischman et al. | |
| 5,980,517 A * | 11/1999 | Gough | 606/41 |
| 6,024,739 A | 2/2000 | Ponzi et al. | |
| 6,063,082 A * | 5/2000 | DeVore | A61B 17/3468 606/170 |
| 6,064,905 A | 5/2000 | Webster, Jr. et al. | |
| 6,085,117 A | 7/2000 | Griffin, III et al. | |
| 6,231,570 B1 | 5/2001 | Tu et al. | |
| 6,572,612 B2 | 6/2003 | Stewart et al. | |
| 6,771,996 B2 | 8/2004 | Bowe et al. | |
| 6,992,477 B2 | 1/2006 | Govari | |
| 7,181,288 B1 * | 2/2007 | Rezai | A61N 1/0534 607/116 |
| 2002/0120261 A1 * | 8/2002 | Morris et al. | 606/41 |
| 2002/0148476 A1 * | 10/2002 | Farley | A61B 18/1492 128/898 |
| 2003/0006759 A1 | 1/2003 | Govari | |
| 2003/0012561 A1 | 1/2003 | Willis | |
| 2003/0125614 A1 * | 7/2003 | Fuimaono et al. | 600/374 |
| 2008/0319436 A1 | 12/2008 | Daniel et al. | |
| 2010/0168737 A1 | 7/2010 | Grunewald | |
| 2010/0222851 A1 * | 9/2010 | Deem | A61B 18/1492 607/72 |
| 2012/0296232 A1 | 11/2012 | Ng | |
| 2012/0296329 A1 * | 11/2012 | Ng | A61B 5/6853 606/41 |

FOREIGN PATENT DOCUMENTS

| | | |
|---|---|---|
| EP | 1 484 011 A2 | 12/2004 |
| EP | 2 641 556 A1 | 9/2013 |
| JP | 2000507844 A | 6/2000 |
| JP | 2003235821 A | 8/2003 |
| JP | 2006320771 A | 11/2006 |
| WO | WO 95/02995 | 2/1995 |
| WO | 9605758 A1 | 2/1996 |
| WO | WO 96/05768 | 2/1996 |
| WO | WO 97/24983 | 7/1997 |
| WO | WO 98/29033 | 7/1998 |

OTHER PUBLICATIONS

"Examination report No. 1 for standard patent application," issued by the Australian Patent Office on Jul. 20, 2017, which corresponds to Australian Patent Application No. 2013273703 and is related to U.S. Appl. No. 13/736,794.

* cited by examiner

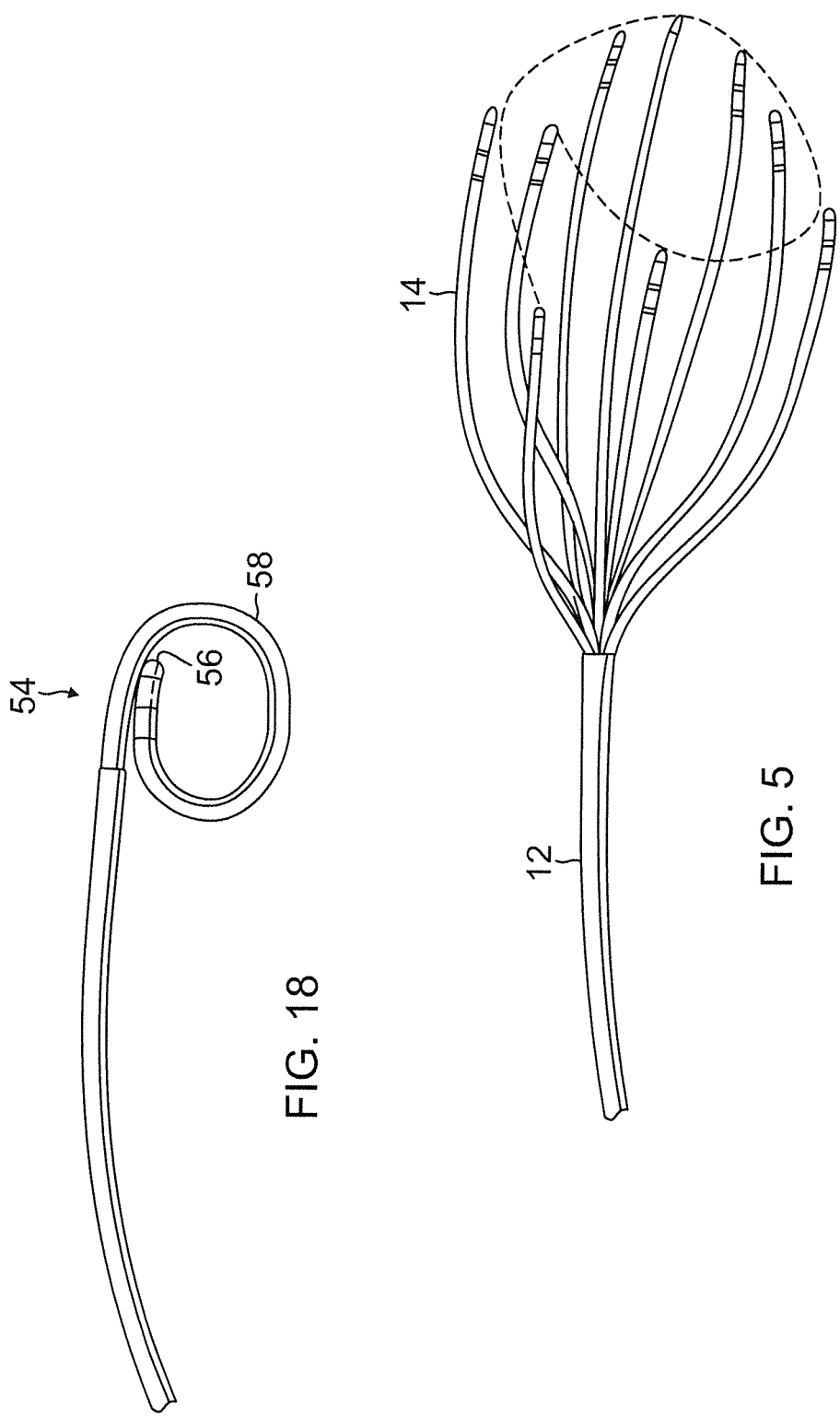

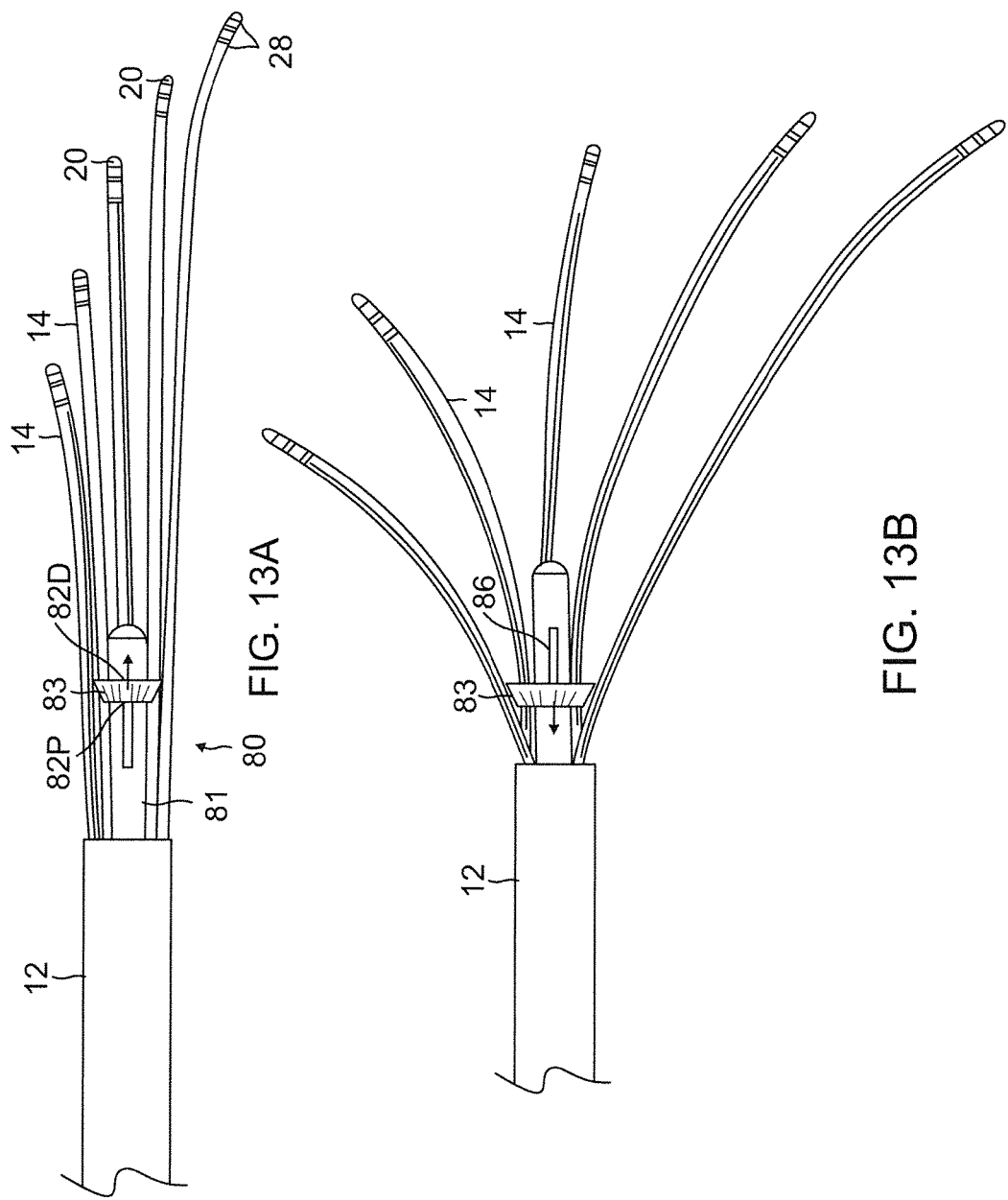

CATHETER WITH MULTIPLE SPINES OF DIFFERENT LENGTHS ARRANGED IN ONE OR MORE DISTAL ASSEMBLIES

FIELD OF INVENTION

The present invention relates to a medical device for use in a vessel of a patient for the purpose of diagnosing or treating the patient, such as mapping tissue and/or ablating tissue using radio frequency (RF) or other sources of energy. More particularly, the invention relates to a catheter with multiple spines, each carrying at least one electrode.

BACKGROUND OF THE INVENTION

Electrode catheters have been in common use in medical practice for many years. They are used to stimulate and map electrical activity in the heart and to ablate sites of aberrant electrical activity. In use, the electrode catheter is inserted into a chamber of the heart. Once the catheter is positioned, the location of aberrant electrical activity within the heart is then located.

One location technique involves an electrophysiological mapping procedure whereby the electrical signals emanating from the conductive endocardial tissues are systematically monitored and a map is created of those signals. By analyzing that map, the physician can identify the interfering electrical pathway. A conventional method for mapping the electrical signals from conductive heart tissue is to percutaneously introduce an electrophysiology catheter (electrode catheter) having mapping electrodes mounted on its distal extremity. The catheter is maneuvered to place these electrodes in contact with or in close proximity to the endocardium. By monitoring the electrical signals at the endocardium, aberrant conductive tissue sites responsible for the arrhythmia can be pinpointed.

Once the origination point for the arrhythmia has been located in the tissue, the physician uses an ablation procedure to destroy the tissue causing the arrhythmia in an attempt to remove the electrical signal irregularities and restore normal heart beat or at least an improved heart beat. Successful ablation of the conductive tissue at the arrhythmia initiation site usually terminates the arrhythmia or at least moderates the heart rhythm to acceptable levels.

A typical ablation procedure involves providing a reference electrode, generally taped to the skin of the patient. RF (radio frequency) current is applied to one or more electrodes on the tip of the catheter, and current flows through the media that surrounds it, i.e., blood and tissue, toward the reference electrode. Alternatively, the catheter may carry bipolar electrodes, in which instance, the current flows from one tip electrode, through the media and toward another electrode carried on the catheter tip. In any case, the distribution of current depends on the amount of electrode surface in contact with the tissue as compared to blood, which has a higher conductivity than the tissue. Heating of the tissue occurs due to electrical current. The tissue is heated sufficiently to cause cellular damage in the cardiac or vascular tissue resulting in formation of a lesion which is electrically non-conductive.

Catheters with multiple spines (commonly referred to as "flower catheters") are known. With each spine carrying at least one electrode, simultaneous contact with multiple locations at a tissue target site is possible for expediting mapping and ablation, especially in a tubular region when lesions or a "line of block" is desired around an inner circumference of the tubular region to interrupt wavelets originating from the tubular region or vessel. With spines having uniform length and arranged in a radial pattern, tissue contact along an inner circumference of the tubular region or vein is readily achieved. A more continuous inner circumference is readily achieved with rotation of the catheter. However, it has been found that ablation along an inner circumference or a narrow band in a vein can lead to vein stenosis, including narrowing, tightening or stiffening of the vein.

Moreover, vessel anatomy comes in all shapes and sizes. Vessel diameters can vary greatly, and abnormally-shaped vessels are sometimes encountered. In these situations, a flower catheter that permits adjustability in the arrangement and positioning of the spines would greatly reduce the time required for perform mapping and/or ablation.

Thus, there is a desire for a catheter adapted for mapping and ablation in a tubular structure that can map or ablate a tubular region which will reduce undesirable damage to the tubular structure. There is a further desire for a flower ablation catheter to provide simultaneous tissue contact to form a line of block without causing stenosis and allow adjustability in the arrangement and/or positioning of the spines.

SUMMARY OF THE INVENTION

The present invention is directed to an improved catheter for mapping and/or ablating tubular regions of the cardiovascular system. The catheter has an elongated catheter body and a distal assembly comprising at least two spines and a mounting assembly with each spine having a proximal end fixed to the mounting assembly and a free distal end. The mounting assembly is coaxial with the longitudinal axis of the catheter and each spine extends radially outwardly from the longitudinal axis of the catheter. The spines can assume an expanded arrangement of many shapes. One shape includes each spine forming an inwardly-curved shape such that each spine contacts an inner tissue wall of a vessel proximal of the distal end of each spine. Another shape includes each spine forming an outwardly-curved shape such that each spine contacts the inner wall of the vessel at the distal end of each spine. Yet another shape includes linear spines such that each spine contacts the inner wall of the vessel at the distal end of each spine.

The length of the spines is varied such that the distal ends of the spines define different circumferences about the inner wall of the vessel. In one embodiment, the length of each spine increases with each spine in a radial progression about the longitudinal axis of the catheter (either clockwise or counterclockwise) between a "start" spine and an "end" spine such that the distal ends of the spines trace a helical pattern with the distal end of the "start" spine defining 0 degrees and the distal end of the "end" spine defining at least about 180 degrees, or preferably at least about 360 degrees.

The catheter of the present invention may include a plunger adapted for telescopic movement relative to the distal assembly along the longitudinal axis of the catheter. The plunger has a tapered side profile with a cam surface for deflecting the spines when the plunger is actuated for telescopic movement relative to the distal assembly by an operator.

The catheter of the present invention may also include a second distal assembly that is distal of a first distal assembly. The second distal assembly may be arranged relative to the first distal assembly such that the distal ends of the spines of the two assemblies define a helical pattern wherein the distal ends of the spines of the first assembly define a proximal portion of the helical pattern and the distal ends of the spines of the second assembly define a distal portion of the helical pattern. For example, the proximal portion may define about 0 to 360 degrees of the helical pattern and the distal portion may define about 360 to 720 degrees of the helical pattern. In accordance with a feature of the invention, the helical pattern minimizes risk of stenosis of the tubular region.

In one embodiment of the present invention, a spatial relationship between the first and second distal assemblies is fixed, such that a separation distance and/or a fixed axial and angular relationship between the distal assemblies are fixed. In another embodiment, the spatial relationship is adjustable by means of a telescopic proximal portion that extends from the second distal assembly and is translatably received in a mounting assembly of the first distal assembly. A puller wire is anchored in the telescopic proximal portion and movement of the puller wire is controlled by an operator via a control handle.

In one embodiment, the catheter includes a catheter body, a distal assembly with at least two spines, each of a different length, and a control handle. Each spine has a support arm with shape memory, a non-conductive covering, at least one electrode. The distal assembly is moveable between an expanded arrangement, in which each spine extends radially outward from the catheter body, and a collapsed arrangement, in which each spine is disposed generally along a longitudinal axis of the catheter body. In one more detailed embodiment, the spines form a curved shape when in the expanded arrangement. Alternatively, each spine forms a substantially straight line.

DESCRIPTION OF THE DRAWINGS

These and other features and advantages of the present invention will be better understood by reference to the following detailed description when considered in conjunction with the accompanying drawings wherein:

FIG. 5 is a distal assembly, in accordance with another alternate embodiment of the present invention.

FIG. 13A is a side view of a distal assembly with a deflection plunger, in accordance with an embodiment of the present invention.

FIG. 13B is a side view of the distal assembly of FIG. 13A, with the deflection plunger deflecting spines of the distal assembly.

FIG. 18 is a side elevational view of a pigtail-shaped dilator suitable for use with a catheter of the present invention.

DETAILED DESCRIPTION OF THE INVENTION

Figure 1:
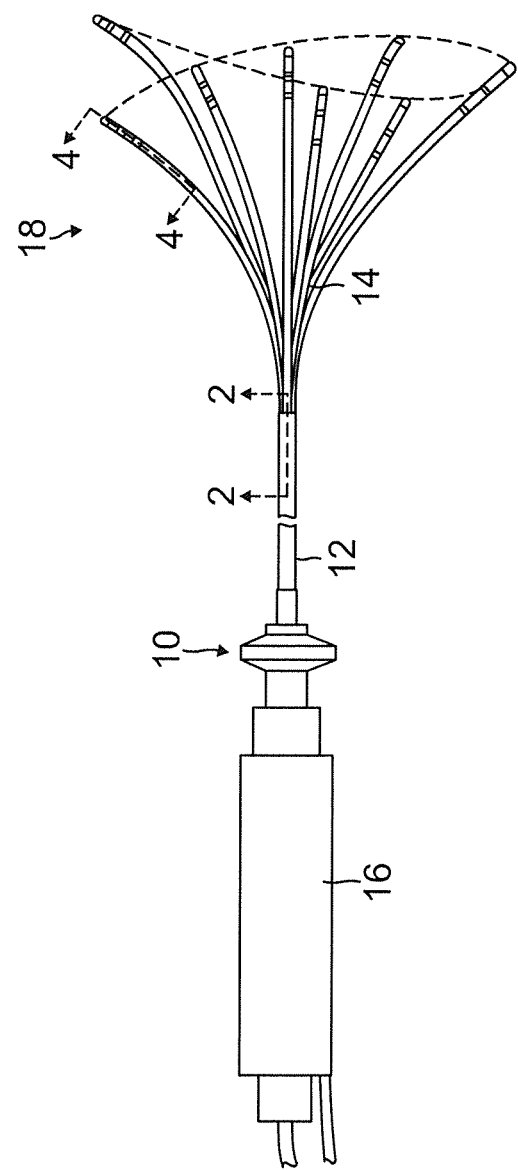
FIG. 1 is a side elevational view of a catheter, in accordance with an embodiment of the present invention.

The invention is directed to a catheter having a distal assembly comprising a plurality of spines. The distal assembly carries at least one position sensor and each spine carries at least one electrode, preferably a tip electrode and at least one ring electrode, such that when the spines are positioned in contact with tissue in a tubular region of cardiovascular tissue, each spine is capable of obtaining electrical, mechanical and locational data for mapping and/or transmitting and receiving electrical energy, e.g., RF energy, for ablating. The spines can assume an expanded arrangement of many shapes. One shape includes each spine forming an outwardly-curved shape such that each spine contacts the inner wall of the vessel at the distal end of each spine (FIG. 1). Another shape includes each spine forming an inwardly-curved shape (FIG. 15) such that each spine contacts an inner tissue wall of a vessel proximal of the distal end of each spine. Yet another shape includes linear spines (FIG. 4) such that each spine contacts the inner wall of the vessel at the distal end of each spine.

As shown in FIG. 1, the catheter 10 comprises an elongated catheter body 12 having proximal and distal ends, a control handle 16 at the proximal end of the catheter body 12, and a distal assembly 18 comprising a plurality of spines 14 mounted at the distal end of the catheter body 12.

Figure 2:
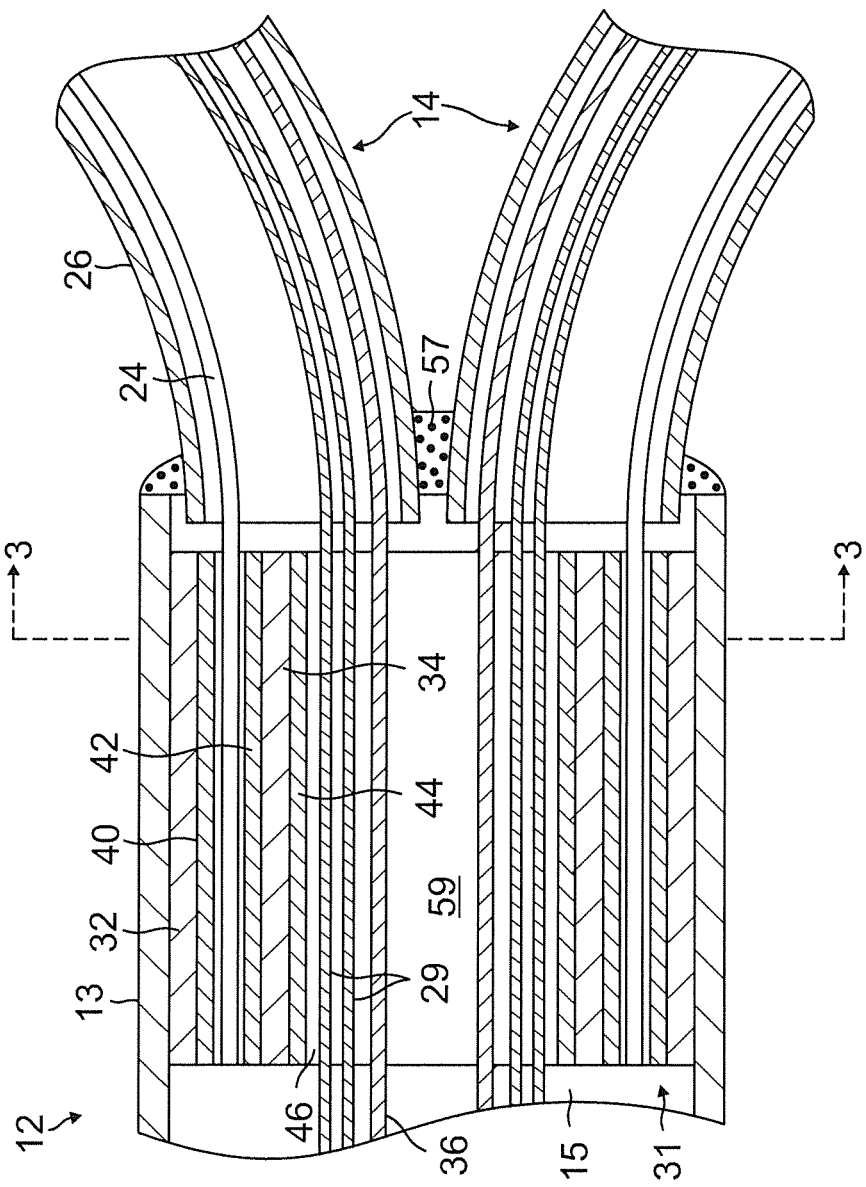
FIG. 2 is a side cross-sectional view of a mounting assembly of a distal assembly, in accordance with an embodiment of the present invention.

As shown in FIGS. 1 and 2, the catheter body 12 comprises an elongated tubular construction having a single, axial or central lumen 15, but can optionally have multiple lumens along all or part of its length if desired. The catheter body 12 is flexible, i.e., bendable, but substantially non-compressible along its length. The catheter body 12 can be of any suitable construction and made of any suitable material. A presently preferred construction of the catheter body 12 comprises an outer wall 13 made of polyurethane or PEBAX® (polyether block amide). The outer wall 13 comprises an imbedded braided mesh of stainless steel or the like, as is generally known in the art, to increase torsional stiffness of the catheter body 12 so that, when the control handle 16 is rotated, the distal end of the catheter body 12 rotates in a corresponding manner.

The length of the catheter body 12 is not critical, but preferably ranges from about 90 cm to about 120 cm, and more preferably is about 115 cm. The outer diameter of the catheter body 12 is also not critical, but is preferably no more than about 8 french, more preferably about 7 french. Likewise, the thickness of the outer wall 13 is not critical, but is preferably thin enough so that the central lumen 15 can accommodate puller wires, lead wires, sensor cables and any other wires, cables or tubes. If desired, the inner surface of the outer wall 13 is lined with a stiffening tube (not shown) to provide improved torsional stability. An example of a catheter body construction suitable for use in connection with the present invention is described and depicted in U.S. Pat. No. 6,064,905, the entire disclosure of which is incorporated herein by reference.

In the depicted embodiment, the distal assembly 18 is comprised of five spines 14. Each spine 14 has a proximal end attached at the distal end of the catheter body 12 and a free distal end, i.e., the distal end is not attached to any of the other spines, to the catheter body, or to any other structure that confines movement of the distal end. Each spine 14 contains a support arm 24 comprising a metal or plastic material that has shape memory, such that the support arm 24 forms an initial shape when no external forces are applied, forms a deflected shape when an external force is applied, and returns to its initial shape when the external force is released. In one embodiment, the support arm 24 comprises a superelastic material, for example a nickel-titanium alloy, such as Nitinol. Each spine 14 also comprises a non-conductive covering 26 in surrounding relation to the support arm 24. In one embodiment, the non-conductive covering 26 comprises a biocompatible plastic tubing, such as a polyurethane or polyimide tubing.

As will be recognized by one skilled in the art, the number of spines 14 can vary as desired depending on the particular application, so that the catheter 10 has at least two spines, preferably at least three spines, more preferably at least five spines and as many as eight or more spines. As described in more detail below, the spines 14 are elastically deflectable and movable between an expanded arrangement, wherein, for example, each spine extends radially outwardly from the catheter body 12, or the spines 14 may be arranged in a collapsed arrangement, wherein, for example, each spine is disposed generally along a longitudinal axis of the catheter body 12 so that the spines are capable of fitting within a lumen of a guiding sheath, as discussed further below.

Moreover, the expanded arrangement of spines 14 can take on various shapes. For instance, in the above-described embodiment, each spine 14 extends radially outwardly from the catheter body 12 and forms an outwardly curved shape as shown in FIG. 1. In another embodiment, shown in FIG. 4, each spine 14 extends radially outwardly from the catheter body 12 and forms a substantially straight line, which is preferably substantially perpendicular to the catheter body 12. In still another embodiment, shown in FIG. 5, each spine 14 bows radially outwardly such that the spines 14, taken together, form a cup shape.

Figure 6B:
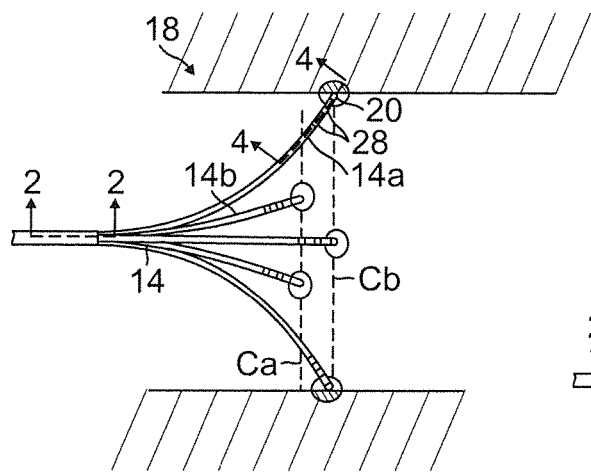
FIG. 6B is a side elevational view of a distal assembly, in accordance with an embodiment of the present invention.
Figure 6C:
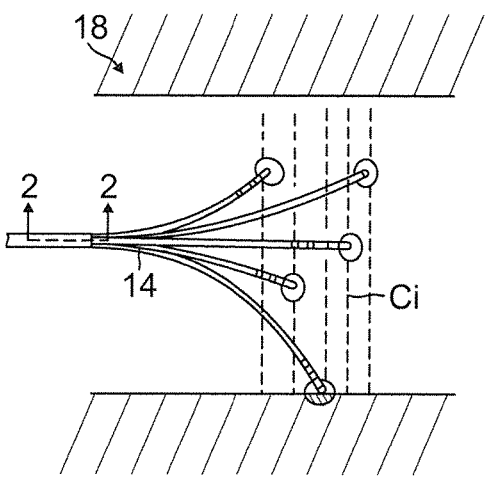
FIG. 6C is a side elevational view of a distal assembly, in accordance with another embodiment of the present invention.
Figure 6D:
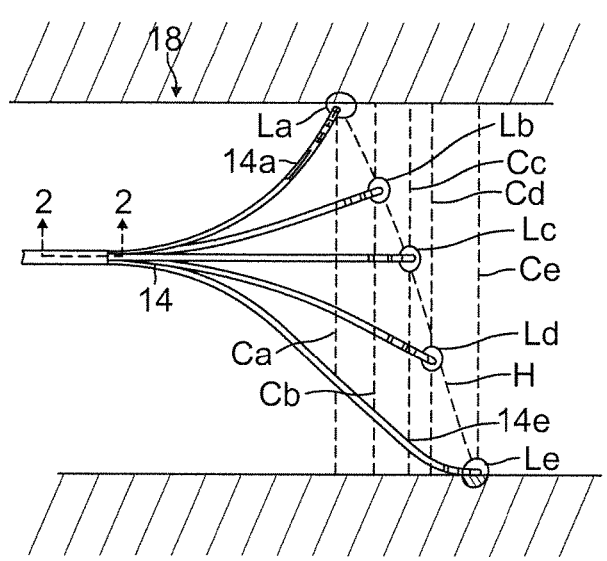
FIG. 6D is a side elevational view of a distal assembly situated in a tubular region of the cardiovascular system, in accordance with an embodiment of the present invention.
Figure 6A:
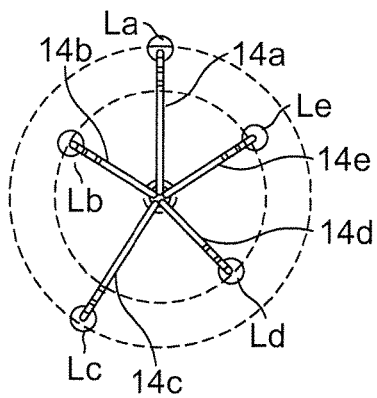
FIG. 6A is an end view of a distal assembly, in accordance with an embodiment of the present invention.

Viewed from the distal end of the catheter body 12 as shown in FIG. 6A, the spines 14 of the distal assembly are arranged in a radial pattern, with each spine having an adjacent spine to its right and an adjacent spine to its left and each spine being generally equally spaced from its adjacent spines. Proximal ends of the spines are held in arrangement in the distal end of the catheter spine by adhesive or glue 57 which also seals the proximal end of the catheter spine. In accordance with a feature of the present invention, the lengths of at least two adjacent spines 14 are different so that their distal ends avoid tracing or defining a common circumference on tissue lining a tubular region of the heart. For example, in FIG. 6B, adjacent spines 14a and 14b define different circumferences Ca and Cb, respectively.

In one embodiment, the length of each spine is unique and different from each of the other spines so that their distal ends avoid tracing a common circumference and instead each traces or defines a different and unique circumference on tissue lining a tubular region of the heart. For example, in FIG. 6C, each spine 14i defines a different circumference Ci.

In particular, the length of each spine starting with a "start" spine 14a with progression in a radial direction (clockwise or counterclockwise) increases with each adjacent spine through an "end" spine 14e such that their distal ends traces a helical pattern on tissue lining a tubular region of the heart. For example, in FIG. 6D, each distal end and its corresponding lesion Li define a different and more distal/deeper circumference Ci tracing helical pattern H. It is understood that while FIG. 6D illustrates a portion (180 degrees) of a helical pattern, a full (360 degrees) helical pattern can be formed under the present invention with the use of additional spines and/or a more radially-dispersed arrangement of the illustrated five spines.

Each of the foregoing spine configurations avoids the distal ends tracing a single common circumference (or radial line) by spreading and dispersing locations of tissue contact longitudinally along the tubular region for the intended purpose of decreasing the risk of stenosis of the tubular region. Accordingly, the locations of tissue contact (and hence resulting ablation sites and lesions L) sufficiently cover the tubular region in terms of radial angles without creating a line of block that lies on a single circumference of the tubular region (FIG. 6A).

Figures 7, 7A:
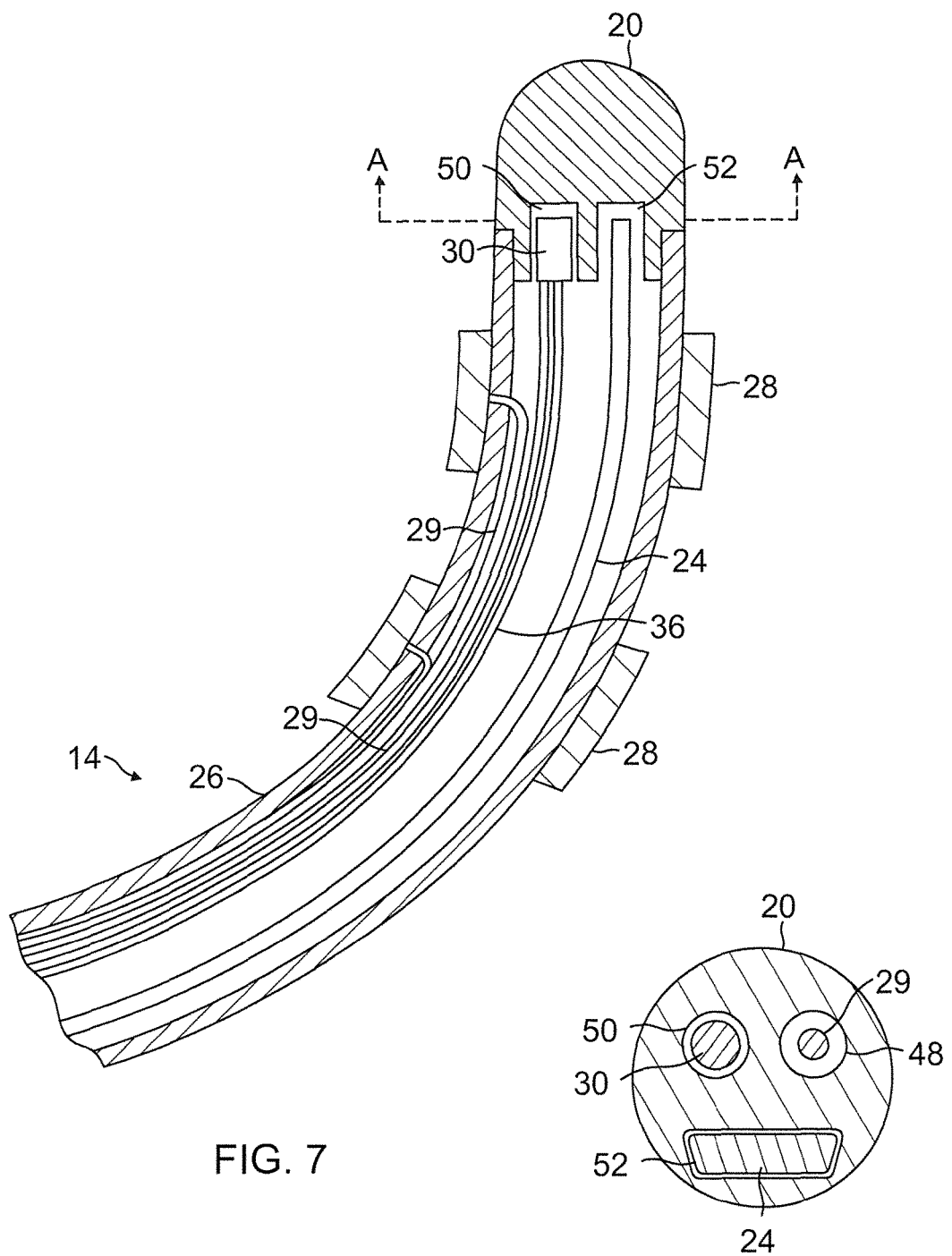
FIG. 7 is a side cross-sectional view of a spine, in accordance with an embodiment of the present invention.
FIG. 7A is an end cross-sectional view of a distal end of the spine of FIG. 7, taken along line A-A.

As shown in FIGS. 7 and 7A, each spine 14 carries at least one electrode mounted along its length, preferably at or near its distal end. In the depicted embodiment, a tip electrode 20 is mounted on a distal end of each non-conductive covering 26 and at least one ring electrode 28 is mounted on each non-conductive covering 26, preferably on the distal end of the non-conductive covering 26. In this bipolar arrangement, the ring electrode 28 is used as a reference electrode. The distance between the tip electrode and ring electrode preferably ranges from about 0.5 mm to about 2 mm. In an alternative bipolar arrangement (not shown), the tip electrode 20 is eliminated and at least two ring electrodes 28 are mounted on each non-conductive covering 26, preferably on the distal end of the non-conductive covering 26. Another alternative embodiment (not shown), is a unipolar arrangement, in which the tip electrode 20 is mounted on the distal end of each non-conductive covering 26, with one or more reference ring electrodes mounted on the distal end of the catheter body 12, or one or more reference electrodes attached outside the body of the patient (e.g., in the form of a patch). In an alternative unipolar arrangement, a ring electrode 28 mounted on each non-conductive covering 26, preferably on the distal end of the non-conductive covering 26, is used instead of a tip electrode 20.

Each tip electrode 20 has an exposed length preferably ranging from about 0.5 mm to about 8 mm, more preferably from about 0.5 mm to about 2 mm, still more preferably about 1 mm. Each ring electrode 28 has a length preferably up to about 2 mm, more preferably from about 0.5 mm to about 1 mm.

Each tip electrode 20 and each ring electrode 28 is electrically connected to an electrode lead wire 29, which in turn is electrically connected to a connector (not shown) at a proximal end of the control handle 16. The connector is connected to an appropriate mapping, monitoring or ablation system (not shown). Each electrode lead wire 29 extends from the connector 17, through the control handle 16, through the central lumen 15 in the catheter body 12, and into the non-conductive covering 26 of the spine 14 where it is attached to its corresponding tip electrode 20 or ring electrode 28. Each lead wire 29, which includes a non-conductive coating over almost all of its length, is attached to its corresponding tip electrode 20 or ring electrode 28 by any suitable method.

The electrodes are manufactured from noble metals that may be used for visualization, recording, stimulation and ablation purposes. Multiple electrodes on a spine would be able to deliver energy in numerous modes. Energy can be delivered to each electrode individually, all electrodes simultaneously, or user selected electrodes only. Energy may be delivered in uni-polar or bi-polar mode. The electrodes may be perforated with a series of holes to facilitate irrigation of the ablation area.

A method for attaching a lead wire 29 to a ring electrode 28 involves first making a small hole through an outer wall of the non-conductive covering 26. Such a hole can be created, for example, by inserting a needle through the non-conductive covering 26 and heating the needle sufficiently to form a permanent hole. The lead wire 29 is then drawn through the hole by using a microhook or the like. The end of the lead wire 29 is then stripped of any coating and welded to the underside of the ring electrode 28, which is then slid into position over the hole and fixed in place with polyurethane glue or the like. Alternatively, each ring electrode 28 may be formed by wrapping the lead wire 29 around the non-conductive covering 26 a number of times and stripping the lead wire of its own non-conductive coating on its outwardly facing surfaces. In such an instance, the lead wire 29 functions as a ring electrode.

Each spine 14 may also include at least one location sensor 30. The location sensor 30 is mounted near the distal end of each spine. In the depicted embodiment, where each spine 14 comprises a tip electrode 20, a location sensor 30 is mounted such that the distal end of the location sensor 30 is secured within its corresponding tip electrode 20, while the proximate end of the location sensor 30 extends into the distal end of the non-conductive covering 26. Each location sensor 30 is used to determine the coordinates of its corresponding tip electrode 20 at each instant when the tip electrode 20 is being used to collect an electrical mapping data point. As a result, both electrical and locational data can be obtained for each data point that is mapped. If the spine 14 carries at least one ring electrode 28 but does not include a tip electrode 20, the location sensor 30 is mounted near the distal end of the non-conductive covering 26, preferably as close to the distal end of the spine 14 as possible or in a plane concentric with the ring electrode 28.

Figure 3:
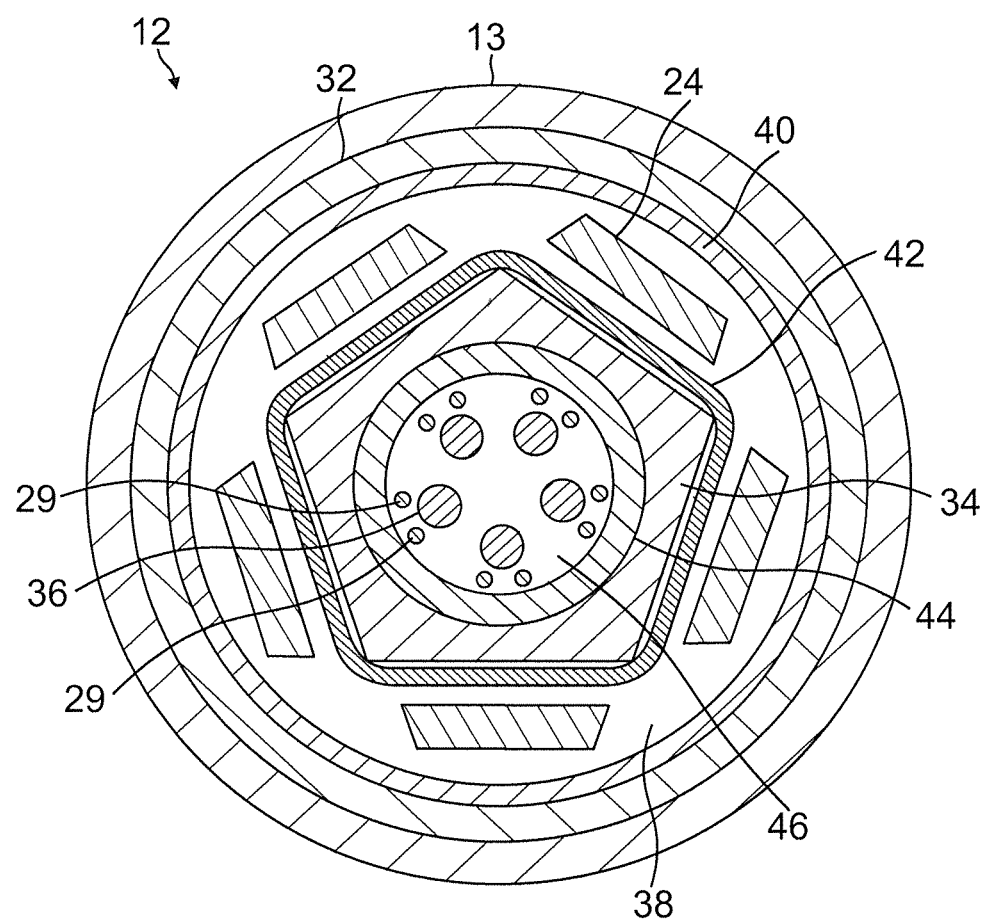
FIG. 3 is an end cross-sectional view of the mounting assembly of FIG. 2, taken along line 3-3.

As shown in FIGS. 2 and 3, each location sensor 30 is connected to a corresponding sensor cable 36. Each sensor cable 36 extends through the non-conductive covering 26, catheter body 12 and control handle 16 and out the proximal end of the control handle 16 within an umbilical cord (not shown) to a sensor control module (not shown) that houses a circuit board (not shown). Alternatively, the circuit board can be housed within the control handle 16, for example, as described in U.S. Pat. No. 6,024,739, the disclosure of which is incorporated herein by reference. Each sensor cable 36 comprises multiple wires encased within a plastic covered sheath. In the sensor control module, the wires of the sensor cable 36 are connected to the circuit board. The circuit board amplifies the signal received from the corresponding location sensor 30 and transmits it to a computer in a form understandable by the computer by means of a sensor connector at the proximal end of the sensor control module. Also, because the catheter 10 is designed for single use only, the circuit board preferably contains an EPROM chip that shuts down the circuit board approximately twenty-four hours after the catheter 10 has been used. This prevents the catheter 10, or at least the location sensors 30, from being used twice.

In one embodiment, each location sensor 30 is an electromagnetic location sensor. For example, each location sensor 30 may comprise a magnetic-field-responsive coil, as described in U.S. Pat. No. 5,391,199, or a plurality of such coils, as described in International Publication WO 96/05768. The plurality of coils enables the six-dimensional coordinates (i.e. the three positional and the three orientational coordinates) of the location sensor 30 to be determined. Alternatively, any suitable location sensor known in the art may be used, such as electrical, magnetic or acoustic sensors. Suitable location sensors for use with the present invention are also described, for example, in U.S. Pat. Nos. 5,558,091, 5,443,489, 5,480,422, 5,546,951, and 5,568,809, and International Publication Nos. WO 95/02995, WO 97/24983, and WO 98/29033, the disclosures of which are incorporated herein by reference. A particularly preferred location sensor 30 is a single axis sensor having a length ranging from about 3 mm to about 7 mm, preferably about 4 mm, such as that described in the U.S. patent application Ser. No. 09/882,125 filed Jun. 15, 2001, entitled "Position Sensor Having Core with High Permeability Material," the disclosure of which is incorporated herein by reference. Smaller sensors are particularly desirable for use in the present invention because of the need to keep the diameters of the spines 14 small enough so that they all fit within the lumen of a guiding sheath. In an alternate embodiment, a single position sensor may be provided at or near a distal end of the catheter body 12, in lieu of a position sensor in each spine.

FIGS. 7 and 7A illustrate a suitable technique for mounting the electrode lead wire 29, the location sensor 30 and the support arm 24 to the tip electrode 20. The electrode lead wire 29 may be secured to the tip electrode 20 by drilling a first blind hole 48, preferably a bore hole, into the tip electrode 20, stripping the lead wire 29 of any coating and placing the lead wire 29 within the first blind hole 48 where it is electrically connected to the tip electrode 20 by a suitable means, such as by soldering or welding. The lead wire 29 may then be fixed in place, for example, by using a polyurethane glue or the like. The location sensor 30 may be similarly fixed in the tip electrode 20. For example, a second blind hole 50, preferably a bore hole, may be drilled into the tip electrode 20 such that the location sensor 30 may be inserted into the second blind hole 50 and affixed therein, for example, using a polyurethane glue or the like. The support arm 24 may also be similarly affixed to the tip electrode 20. For example, a third blind hole 52, preferably a bore hole, may be drilled into the tip electrode 20 such that the support arm 24 may be inserted into the third blind hole 52 and affixed therein, for example, using a polyurethane glue or the like. Alternatively, a single blind hole (not shown) in the proximal end of the tip electrode 20 can be used for mounting the location sensor 30 and support arm 24, and the distal end of the lead wire 29 can be wrapped around the outside proximal end of the tip electrode, which is not exposed and attached by solder, welding or any other suitable technique. Any other arrangement for mounting these components in the spine could also be used.

A suitable construction of the distal end of the catheter body 12, having spines 14 mounted thereto, is depicted in FIGS. 2 and 3. For clarity, only two spines 14 are shown in FIG. 2. Mounted in the distal end of the lumen 15 of the catheter body 12 is a spine mounting assembly 31. The spine mounting assembly 31 comprises an outer mounting ring 32 disposed within the outer wall 13 of the catheter body 12. The outer mounting ring 32 preferably comprises a metal material, such as stainless steel, more particularly stainless steel 303, and may be attached at the distal end of the catheter body 12 by a variety of methods, such as by welding or by use of an adhesive, such as a polyurethane glue. Alternatively, the outer mounting ring 32 may comprise a plastic material. A mounting structure 34 is provided coaxially within the outer mounting ring 32. In the depicted embodiment, the mounting structure 34 is multi-sided and comprises a metal material, such as stainless steel, more particularly stainless steel 303. The mounting structure 34 may also alternatively comprise a plastic material. The outer mounting ring 32 and the mounting structure 34 provide a channel 38 in which the proximal end of each support arm 24 is mounted. Specifically, each spine 14 is mounted in the catheter body 12 by removing a portion of the non-conductive covering 26 at the proximal end of each spine 14, inserting the distal end of each support arm 24 into the channel 38 between the outer mounting ring 32 and the multi-sided mounting structure 34 and affixing each support arm 24 within the channel 38 by any suitable means, such as with a polyurethane glue or the like.

In one embodiment, the support arm 24 has a generally trapezoidally-shaped end cross section with curved sides. In such an arrangement, when each support arm 24 is inserted into the channel 38, a substantially flat surface of each support arm 24, preferably the base of the trapezoidally-shaped end cross section, is mounted against a substantially flat surface on the multi-sided mounting structure 34. Preferably the number of substantially flat outer surfaces on the multi-sided mounting structure 34 corresponds to the number of spines 14. In such an instance, the support arm 24 of each spine 14 may be mounted within the channel 38 and adjacent to its corresponding side on the multi-sided mounting structure 34 to enable the support arms 24, and thus the spines 14, to be equally spaced around the multi-sided mounting structure 34. The multi-sided mounting structure 34 may be approximately co-axial with the longitudinal axis of the catheter body 12 such that the spines 14 are equally spaced about the catheter body 12 as well. Once each support arm 24 is properly positioned within the channel 38, each support arm 24 may be affixed within the channel 38 by any suitable means, such as by use of an adhesive, such as a polyurethane glue. Alternatively, the mounting structure 34 can have a round outer surface, although with such an embodiment more care needs to be taken if the support arms 24 are to be evenly spaced about the mounting structure.

In the depicted embodiment, a first non-conducting tube 40 is disposed between the outer mounting ring 32 and the support arms 24, and a second non-conducting tube 42 is disposed between the support arms 24 and the mounting structure 34. The non-conducting tubes 40 and 42, which may be polyimide tubes, ensure that each support arm 24 remains electrically isolated. In addition, a mounting ring inner tube 44 is secured within the mounting structure 34. The mounting ring inner tube 44 preferably comprises a non-conducting material such as polyimide. The mounting ring inner tube 44 defines a mounting ring lumen 46 through which each of the electrode lead wires 29 and sensor cables 36 extend.

Figure 4:
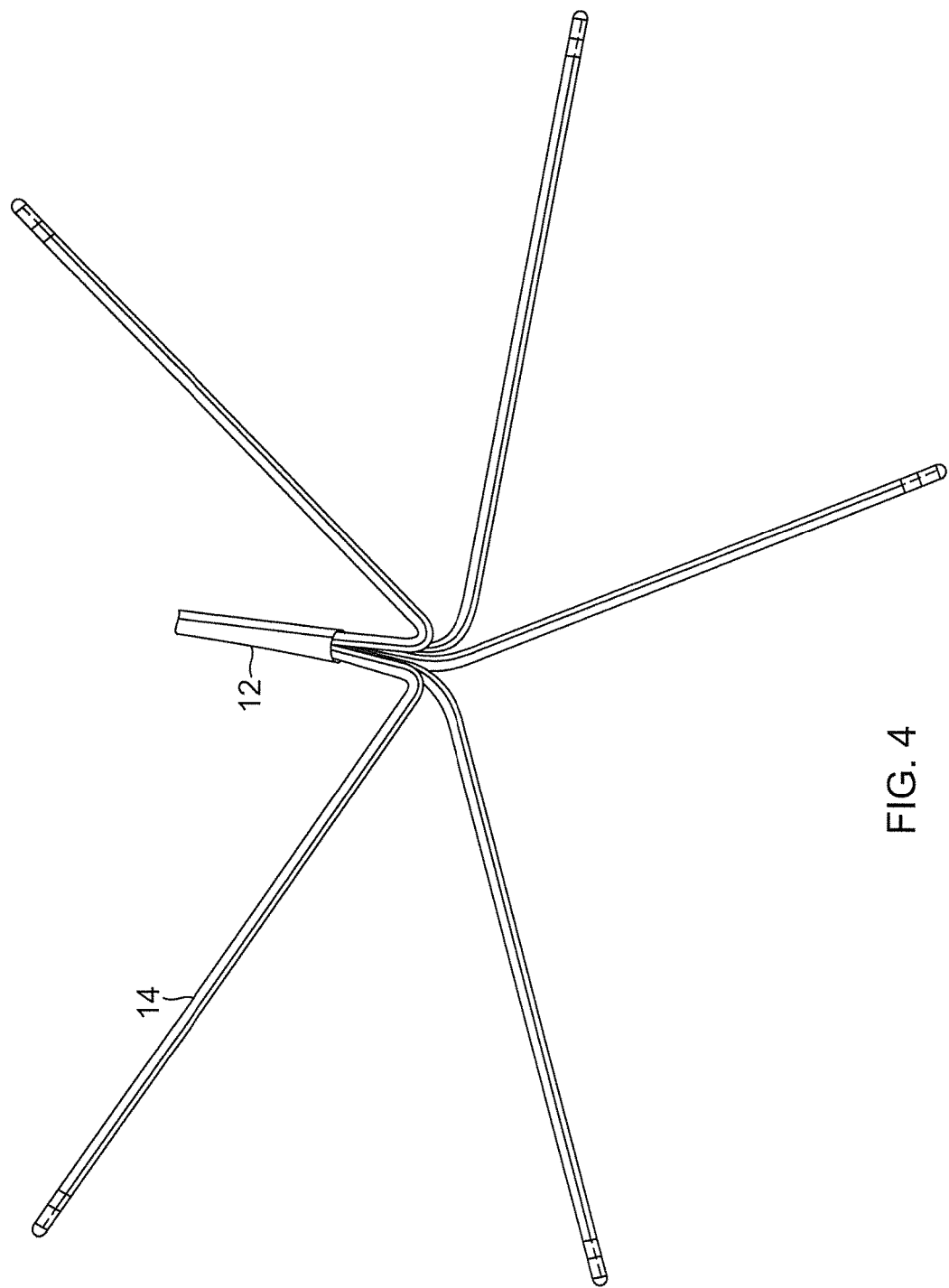
FIG. 4 is a distal assembly, in accordance with an alternate embodiment of the present invention.

As previously discussed, when mounting the support arms 24 to the spine mounting assembly 31, a portion of the non-conductive covering 26 at the proximal end of each spine 14 is removed to expose the support arm 24. Removing a portion of the non-conductive covering 26 at the proximal end of each spine 14 enables the electrode lead wires 29 and sensor cables 36, corresponding to each tip electrode 20, ring electrode 28 and location sensor 30, to extend from the lumen 15 of the catheter 12, through the mounting ring lumen 46, and into each non-conductive covering 26. As shown in FIG. 4, once inserted into the non-conductive coverings 26, the electrode lead wires 29 and sensor cables 36 extend within the non-conductive covering 26 and are electrically connected at their distal ends to their corresponding tip electrode 20, ring electrode 28 or location sensor 30.

Figure 8:
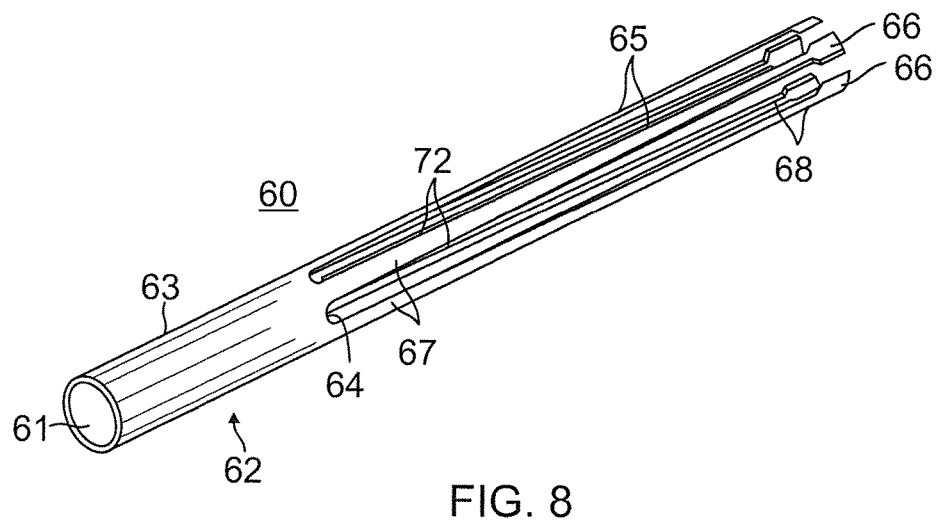
FIG. 8 is a perspective view of a unibody support member, in accordance with an embodiment of the present invention.
Figure 9:
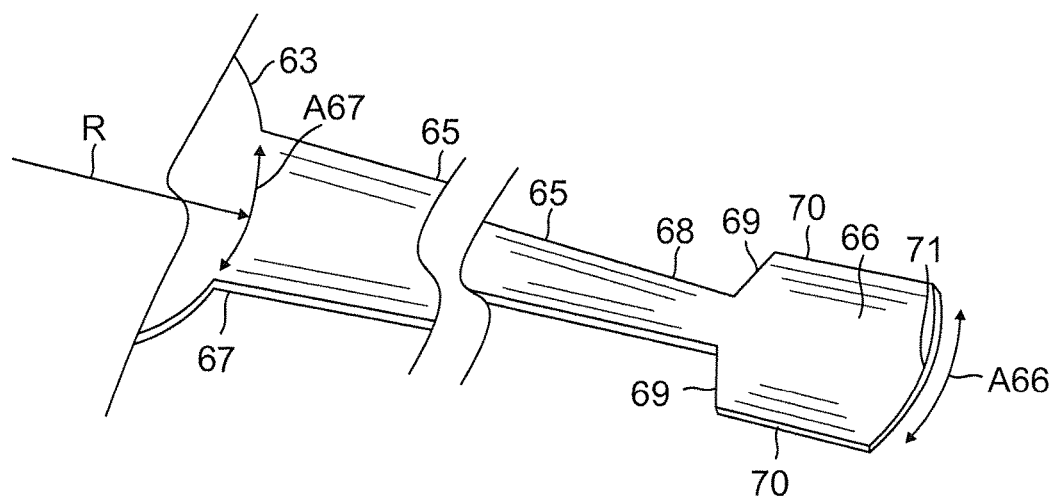
FIG. 9 is a perspective view of a stem portion of the unibody support member of FIG. 8.

In an alternate embodiment, the support arms 24 are provided on a unibody support member 60 is provided as shown in FIGS. 8 and 9. The member 60 has a proximal mounting portion 62 from which the support arm 24 extend longitudinally from a distal edge 64 of the mounting portion 62. The mounting portion 62 has an open cylindrical body 63 defining a lumen 61 therethrough and each spine has an elongated tapered stem 65 and an enlarged distal portion 66. The stem 65 has a wider proximal end 67 and a narrower distal end 68. The enlarged distal portion 66 has a curvature defined by a radius R of the cylindrical body 63 of the mounting portion 62, and a generally rectangular or "paddle" shape with angled proximal edges 69, non-parallel divergent side edges 70 and a straight distal end 71. In the disclosed embodiment, a curved width or arc A66 of enlarged distal portion 66 is advantageously greater than a curved width or arc A67 of the proximal end of the spine stem. The longer arc A67 at the distal portion of each of the arm 24 creates a large anchoring point that helps keep the non-conductive covering 26, and in turn the ring electrodes 28, in place. The narrower and tapered stem 65 between the mounting portion 62 and the enlarged distal portion 66 allows each spine 14 to be very flexible. In one embodiment, the unibody support member 60 is formed from an elongated cylinder that is cut (e.g., laser cut) longitudinally at 72 to form each stem and spine.

Figures 10, 10A:
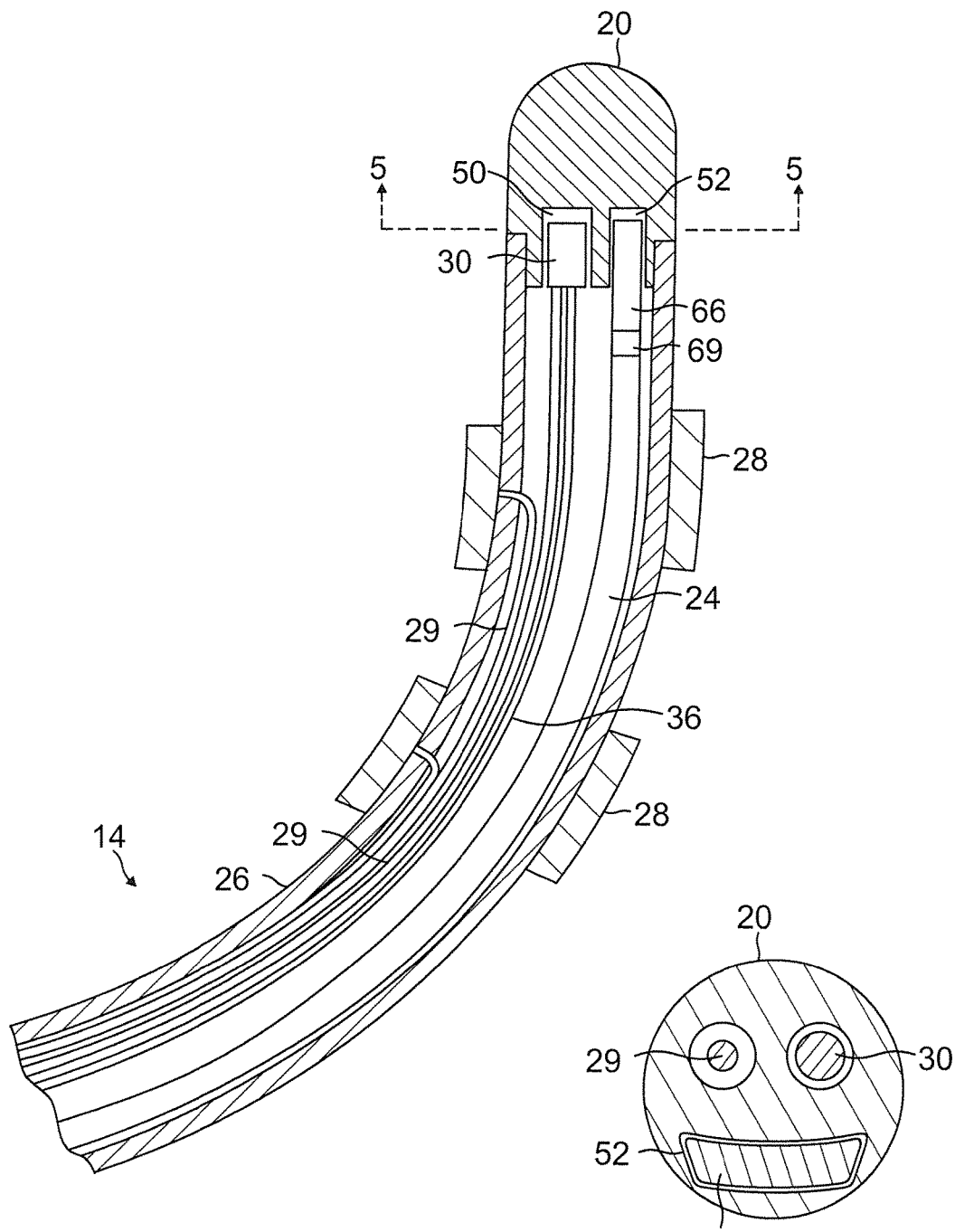
FIG. 10 is a side cross-sectional view of a spine of a distal assembly using a unibody support member, in accordance with an embodiment of the present invention.
FIG. 10A is an end cross-sectional view of a distal end of the spine of FIG. 10, taken along line A-A.

The nonconductive covering 26 is mounted on each spine in a similar manner as described above in the embodiment of FIG. 2 with individual and separate spines 14. FIGS. 10 and 10A illustrate a similar technique for mounting the electrode lead wires 29, the location sensors 30 and the support arms 24 to the tip electrodes 20 of the spines of the unibody spine member 60. Blind holes 48, 50 and 52 are formed in the tip electrode 20, except the blind hole 52 has a curved trapezoidal suited to the cross-sectional shape of the enlarged distal portion 66 of the spine.

Figure 11:
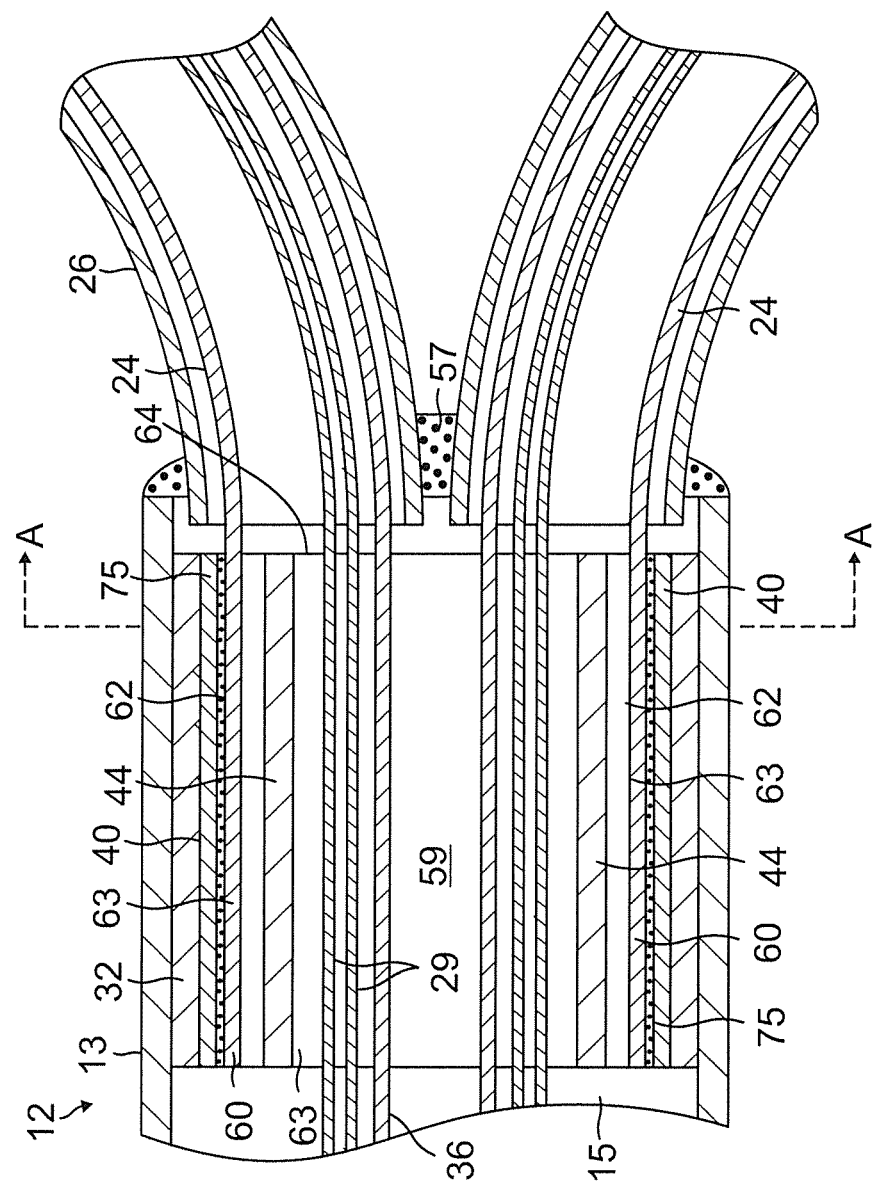
FIG. 11 is a side cross-sectional view of a mounting assembly using a unibody support member, in accordance with an embodiment of the present invention.
Figure 11A:
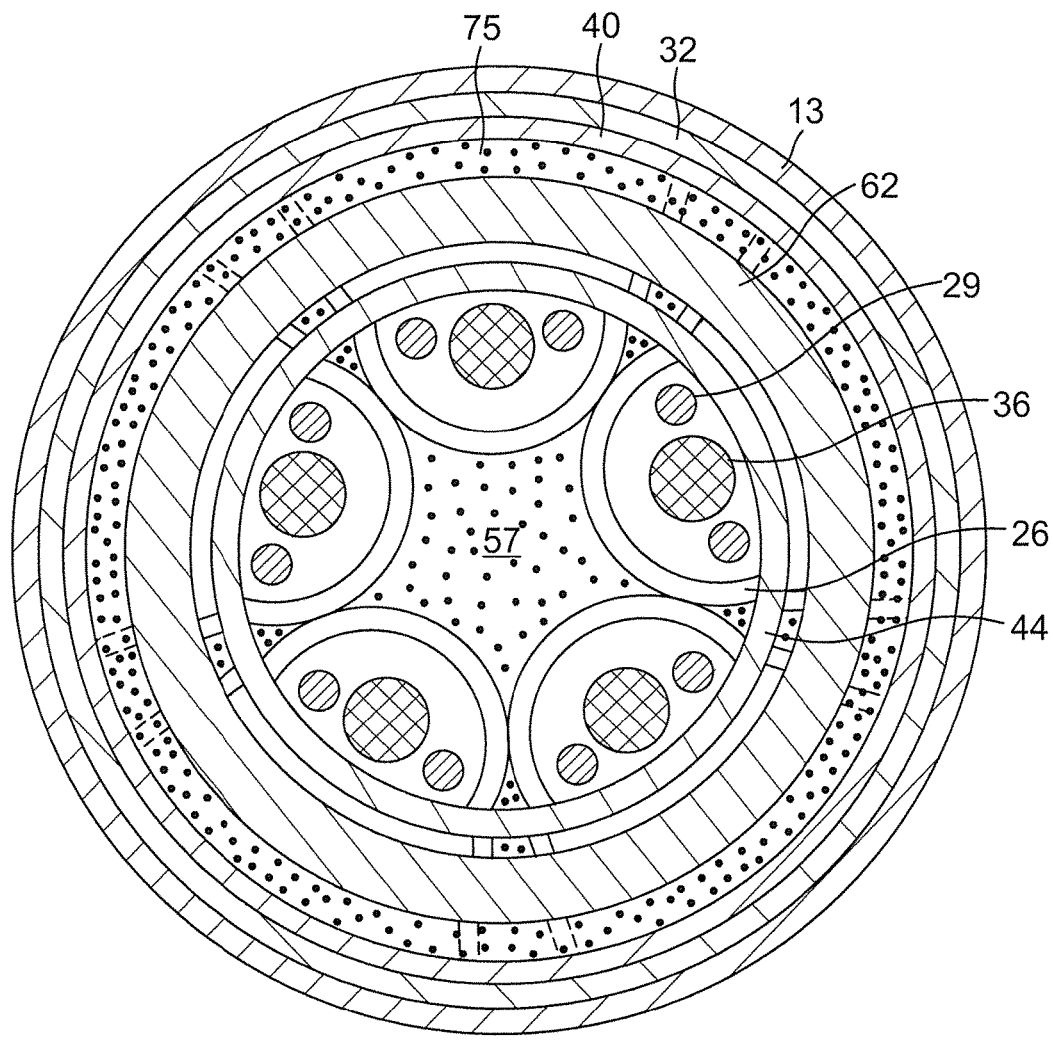
FIG. 11A is an end cross-sectional view of the mounting assembly of FIG. 11, taken along line A-A.

A suitable construction of the distal end of the catheter body 12, having the unibody support member 60 mounted thereto, is depicted in FIGS. 11 and 11A. For clarity, only two spines 14 are shown in FIG. 11. Mounted in the distal end of the lumen 15 of the catheter body 12 is the unibody support member 60. The cylindrical body 63 of the proximal mounting portion 62 is disposed between the first nonconductive tubing 40 and the mounting ring inner tube 44. The mounting portion 62 may be attached at the distal end of the catheter body 12 by a variety of methods, such as by welding or by use of an adhesive, such as a polyurethane glue 75. The lead wires 29 and sensor cable 36 for each spine 14 pass through the lumen 61 lined by the inner tube 44. The cylindrical body 63 advantageously secures and anchors the proximal ends of the support arms 24 in the distal end of the catheter body 12 and also secures and anchors each arm relative to each other radially about the distal end of the catheter body 12.

Figure 12:
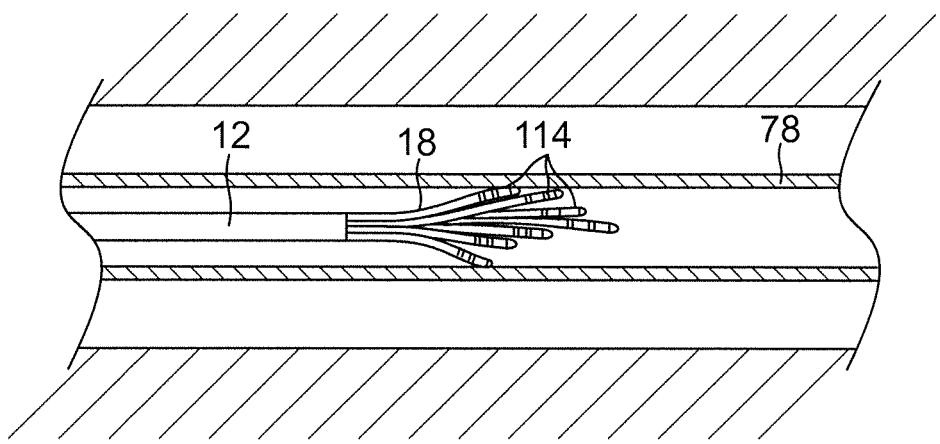
FIG. 12 is a side view of a catheter of the present invention situated in a guiding sheath, in accordance with an embodiment of the present invention.

Regardless of the form and structure of the support arms 24, movement of the spines 14 between the expanded and collapsed arrangements may be accomplished by a number of different means. For example, the distal assembly 18 may be fed through a guiding sheath 78 in the collapsed arrangement (FIG. 12) where a compression force is applied by the guiding sheath as the distal assembly is advanced to the tissue target site. When the guiding sheath is moved proximally relative to the distal end of the catheter to expose the spines 14, the compression force is no longer applied by the guiding sheath on the spines and the shape memory of the support arms 24 allows the support arms to revert to an expanded arrangement. In the expanded arrangement, at least one electrode from each spine 14 can be placed into contact with tissue at a plurality of locations, as shown in FIGS. 6B, 6C and 6D.

Figure 13C:
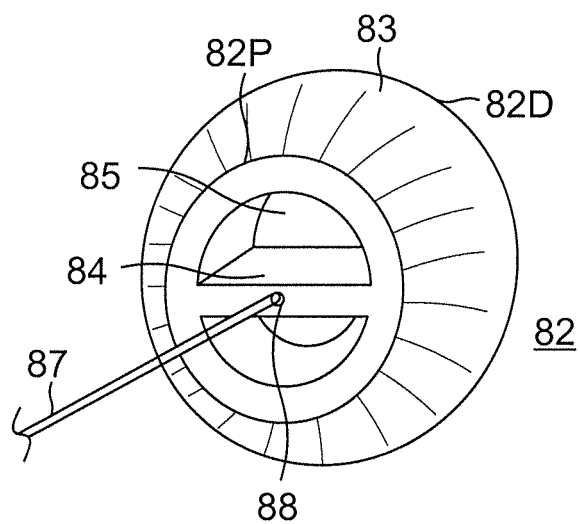
FIG. 13C is a perspective view of a plunger head in accordance with an embodiment of the present invention.

Movement between the expanded and collapsed arrangements may also be accomplished or aided by a plunger 80 as illustrated in FIGS. 13A-13C. Extending centrally and longitudinally from the distal end of the catheter, the plunger 80 has an elongated, hollow cylindrical body 81 and a movable distal plunger head 82 that is shaped as an enlarged ring with a tapered side profile that is longitudinally slidable on an outer surface of the body 81. The body 81 extends from the distal end of the catheter. In the embodiments of FIGS. 2 and 11, the body 81 can extend from central area 59 such that the body 81 is surrounded radially by the lead wires 29 and the sensor cables 36 from the spines 14.

The tapered ring shape of plunger head 82 has a central opening 85 and smaller proximal end 82P and a larger distal end 82D (FIG. 13C) as defined by an increasing diameter which provides an angled cam surface 83 that comes into contact and acts on the spines 14 to spread them apart radially when the plunger head 82 is drawn proximally toward the distal end of the catheter body 12. As illustrated in FIGS. 13C and 13D, the central opening 85 is bridged by a cross-bar 84 that sits in opposing slots 86 formed in the body 81 of the plunger 80. Distal end of a puller wire 87 is anchored in the cross-bar 84, for example, a blind hole 88 formed in a proximal face of the cross-bar 84. The puller wire 87 extends through the body 81 of the plunger 80, through the central lumen 15 of the catheter body 12 and into the control handle 16 where it is acted upon by an actuator (not shown) provided on the control handle. A user manipulating the actuator can draw the puller wire 87 proximally or advance it distally to slide the plunger head 82 longitudinally on the body 81 to, respectively, move the spines 14 into the expanded arrangement (FIG. 13B) or allow the spines to return to their collapsed arrangement (FIG. 13A).

Figure 14:
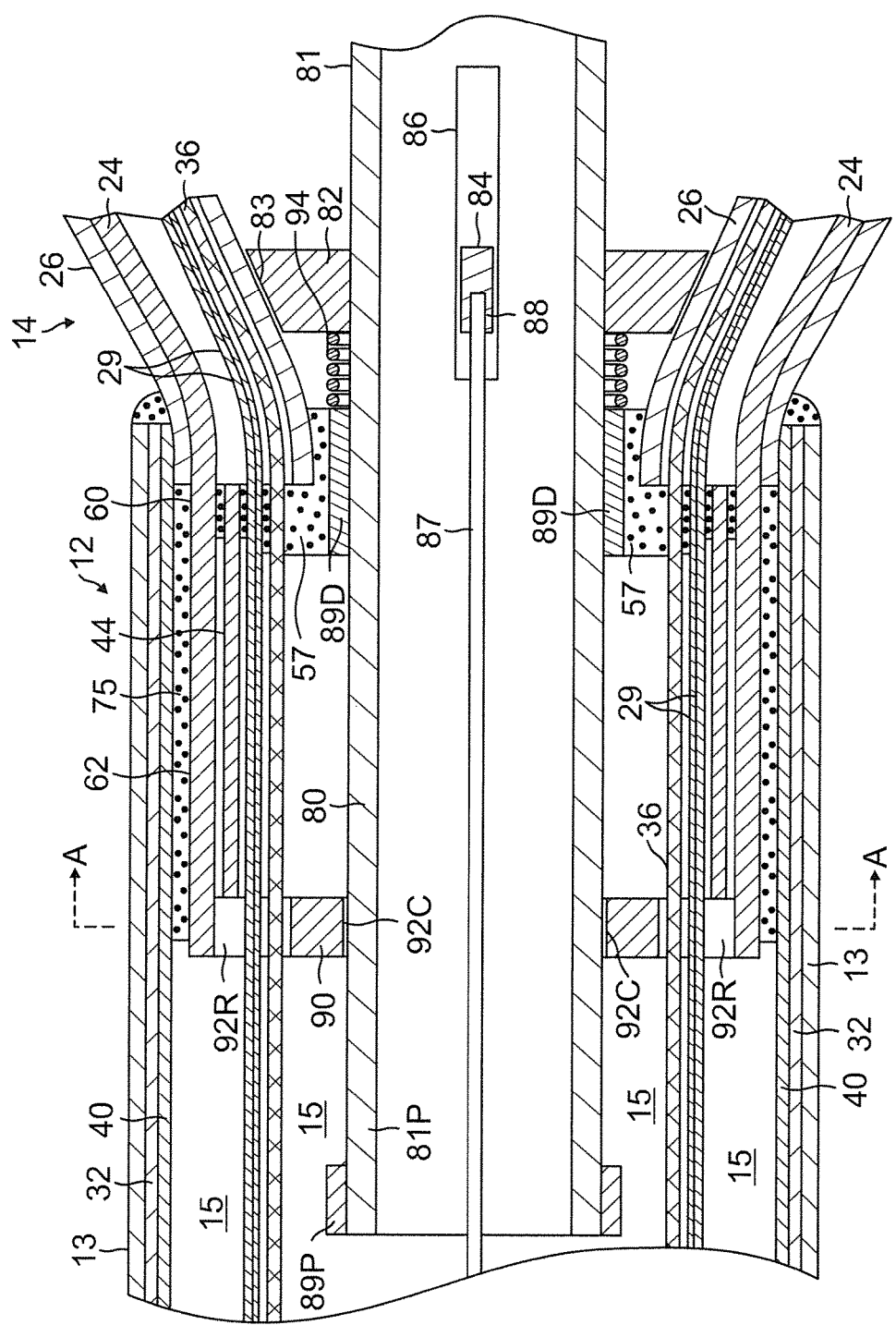
FIG. 14 is a side cross-sectional view of the distal assembly of FIG. 13B.
Figure 14A:
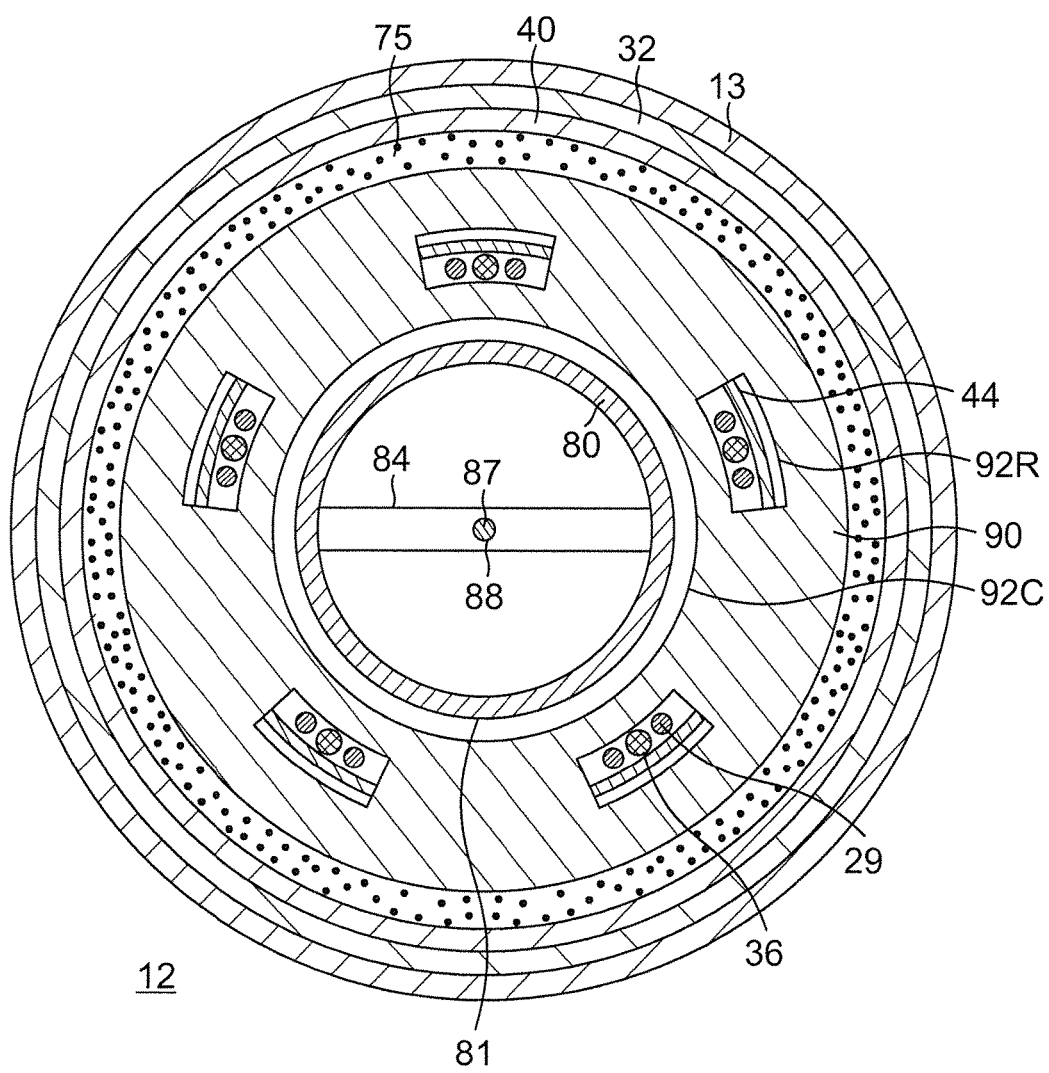
FIG. 14A is an end cross-sectional view of the distal assembly of FIG. 14, taken along line A-A.

In a more detailed embodiment of FIG. 14, the plunger 80 is biased to move into the collapsed arrangement by a spring 94 (shown compressed in FIG. 14) mounted on the body 81 of the plunger 80 between the distal plug 57 and the plunger head 82. A proximal end of the spring 94 abuts against a distal annular stop member 89D affixed to the distal assembly 18 by the plug 57. The distal end of the body 81 extends through the stop 89D and is slidably supported and guided by the stop 89D. The spring 94 resists compression and therefore provides a distally-directed force on the plunger head 82 in the absence of a proximally-directed force applied on the plunger head 82 by means of the puller wire 87. Moreover, as shown in FIG. 14A, a proximal end of the unibody support member 60 may include a proximal end plate 90 with through hole(s) or slot(s) 92R and 92C arranged radially and centrally to support components and/or allow passage of components through the plate 90. In the illustrated embodiment, the end plate 90 has the center through-hole 92C through which a proximal end 81P of the plunger body 81 is received and translatably supported. A proximal annular stop member 89P is provided at the proximal end 81P to limit the distal movement of the plunger body 81 to prevent it from disengaging from the plate 90. The plurality of radially arranged slots 92R are provided in the plate 90 to allow passage of the lead wires 29 and sensor cables 36.

Figure 15:
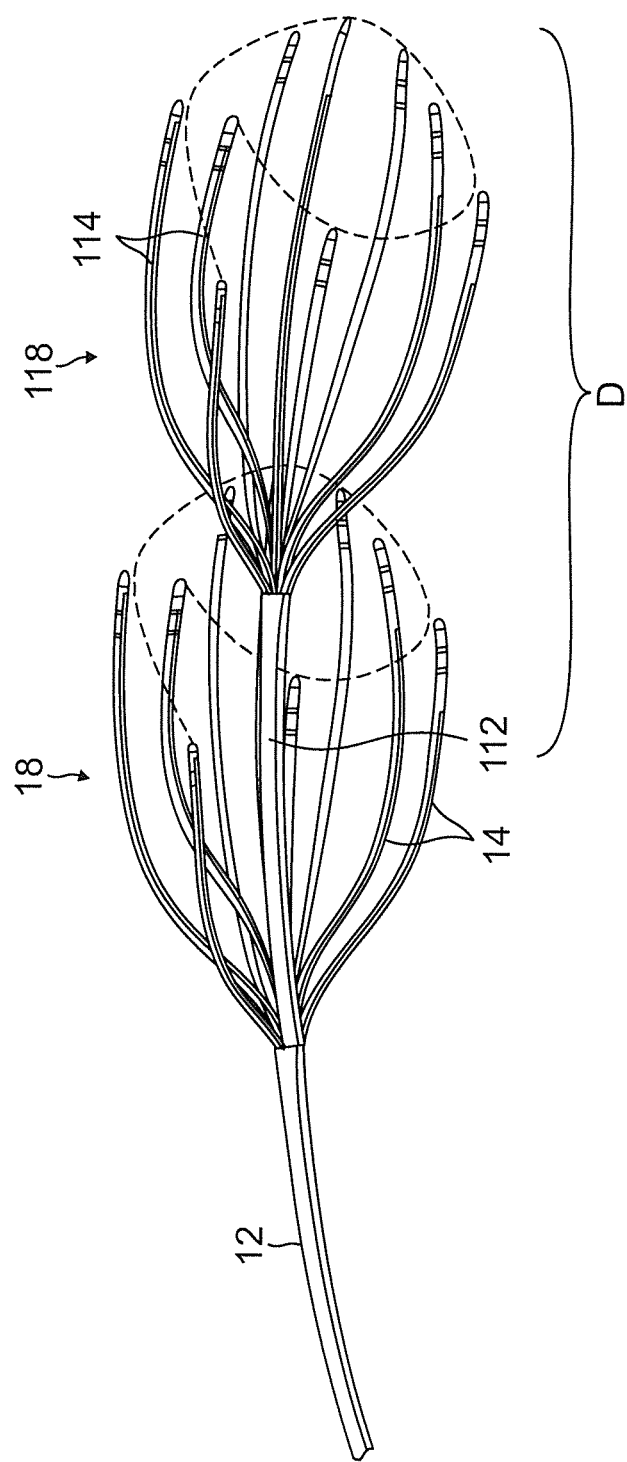
FIG. 15 is a side view of a catheter with two distal assemblies, in accordance with an embodiment of the present invention.

In accordance with another feature of the present invention, a catheter 110 is illustrated in FIG. 15 having first and second distal assemblies 18 and 118, wherein the second distal assembly 118 is distal of the first distal assembly 18. The description above of the distal assembly 18 is incorporated herein in relation to the second distal assembly 118, wherein similar or counterpart components between the first and second distal assemblies are identified by reference numerals sharing the same last two digits, e.g., 18 and 118. The second distal assembly 118 also has a plurality of spines 114 constructed in a similar manner to the spines 14 of the first distal assembly 18. However, it is understood that variations between the distal assemblies 18 and 118 may be appropriate for selected applications and uses. For example, the distal assemblies may have different plurality of spines, different lengths of spines and/or different arrangements of spines.

Figure 2A:
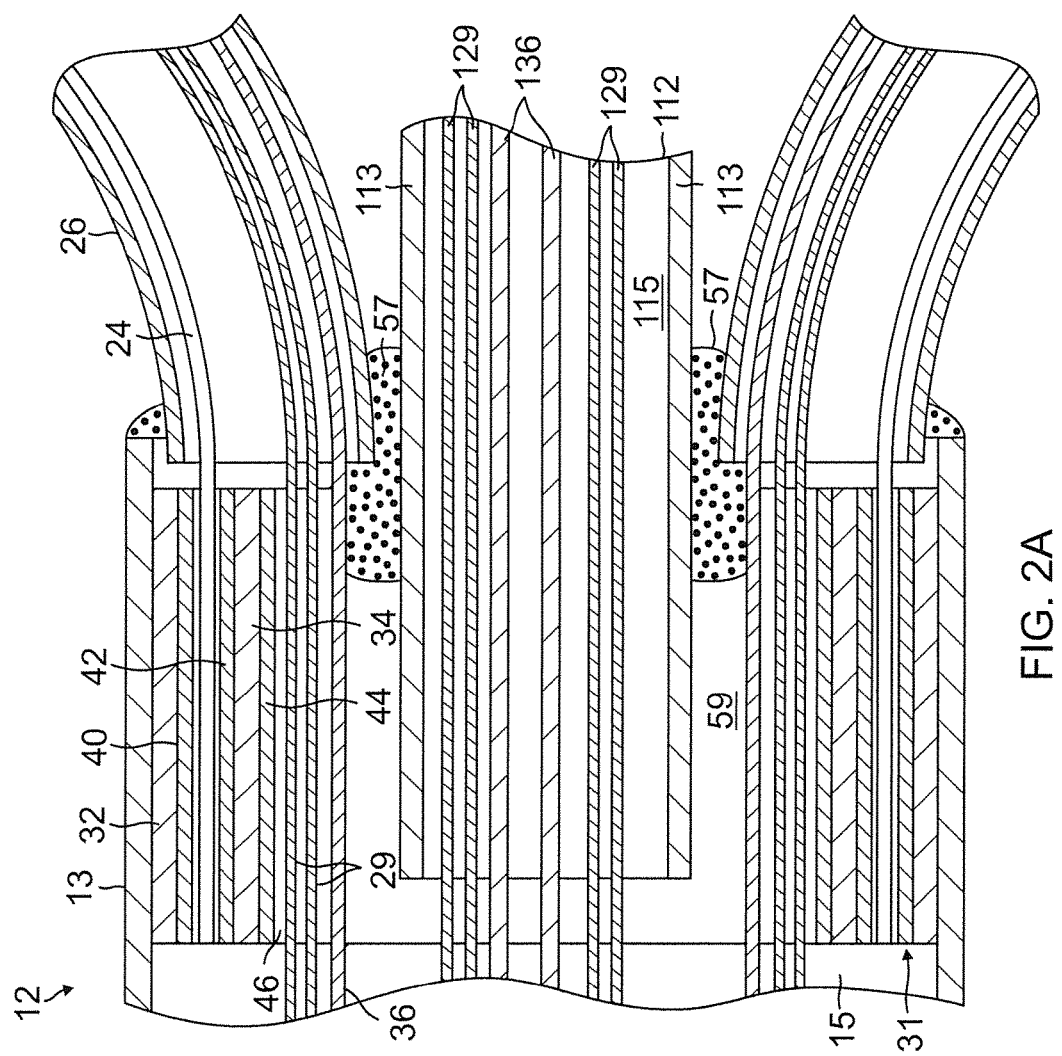
FIG. 2A is a side cross-sectional view of a junction between a first distal assembly and a proximal end of a second distal assembly, in accordance with an embodiment of the present invention.
Figure 2B:
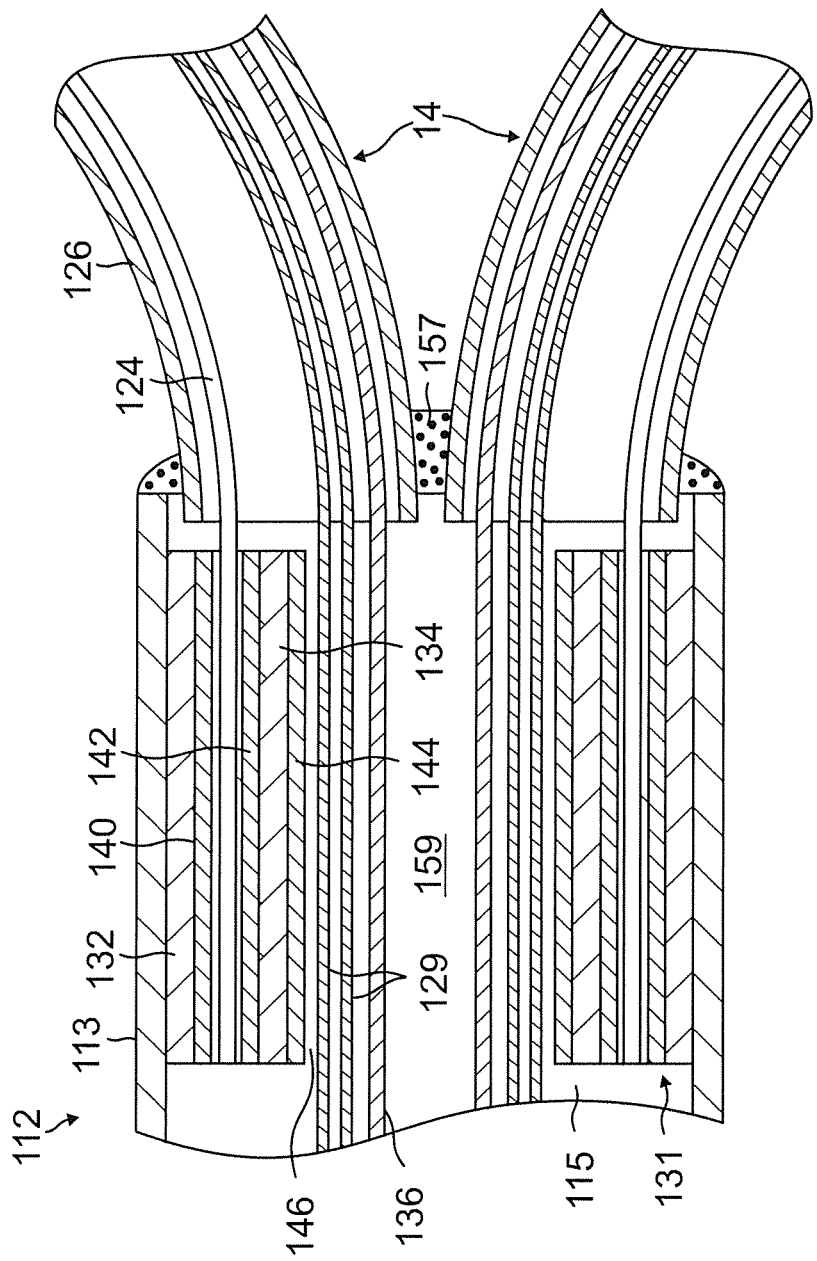
FIG. 2B is a side cross-sectional view of a second distal assembly suitable for use with the first distal assembly of FIG. 2A, in accordance with an embodiment of the present invention.
Figure 11B:
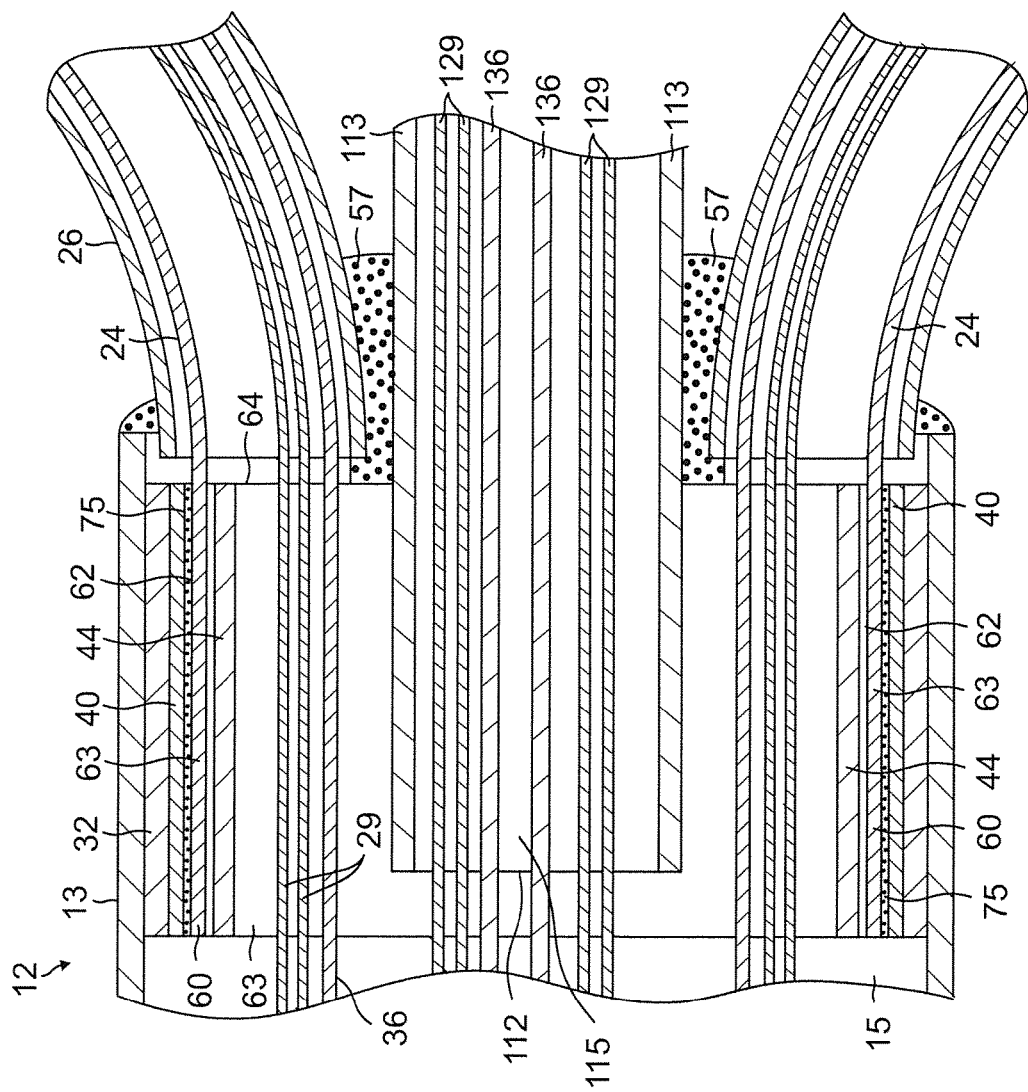
FIG. 11B is a side cross-sectional view of a junction between a first distal assembly and a proximal end of a second distal assembly, in accordance with another embodiment of the present invention.
Figure 11C:
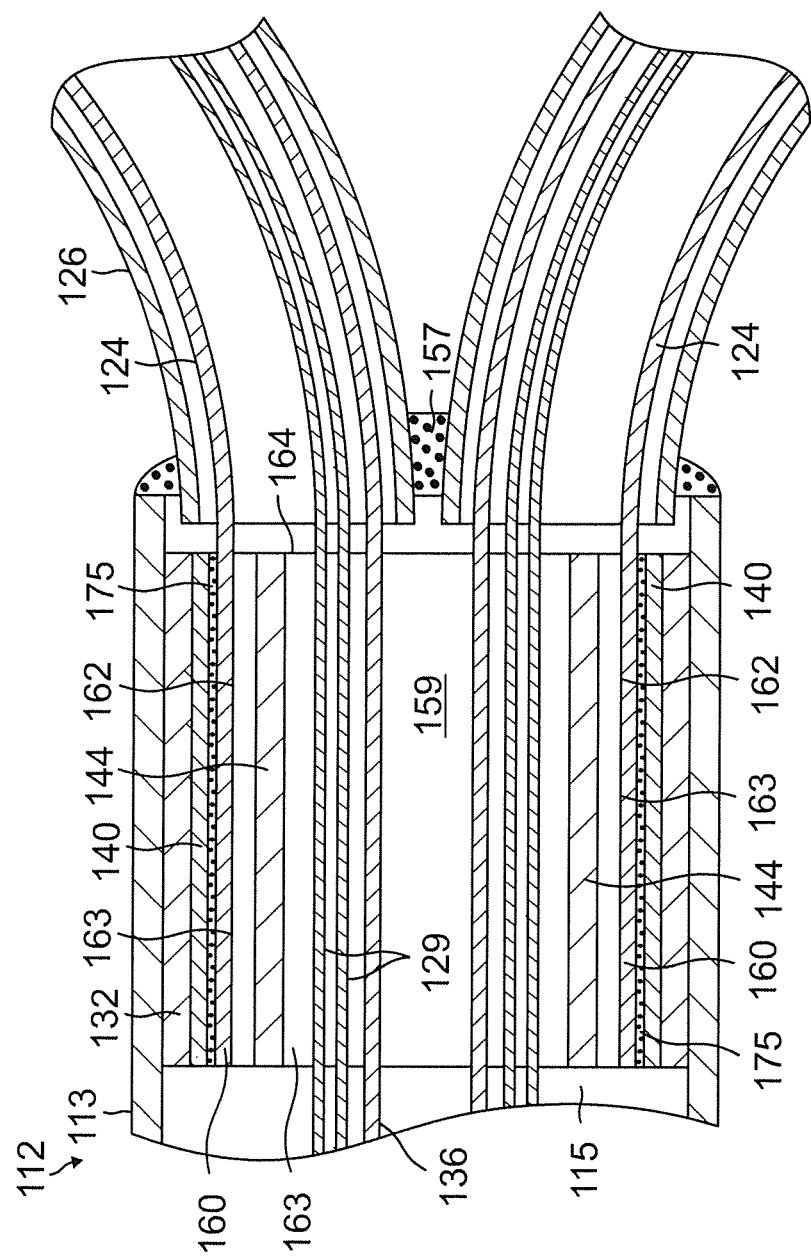
FIG. 11C is a side cross-sectional view of a second distal assembly suitable for use with the first distal assembly of FIG. 11B, in accordance with an embodiment of the present invention.

With reference to FIGS. 2, 2A, 11 and 11B, the second distal assembly 118 has an elongated straight proximal portion 112 that extends from the distal end of the catheter body 12. In the illustrated embodiment, the straight proximal portion 112 has a construction similar to that of the catheter body 12, with an outer wall 113 providing a central lumen 115, except with a smaller diameter. In one embodiment, the portion 112 remains in a fixed relationship with the catheter body 12 such that the distal assemblies 18 and 118 remain in a fixed relationship with each other, including a fixed spatial relationship, a fixed separation distance and/or a fixed axial and angular relationship with each other. Embodiments of a junction between the catheter body 12 and the portion 112 suitable for use with the catheter body 12 and distal assembly 18 of FIGS. 2 and 11 are illustrated in FIGS. 2A and 11B, respectively, with similar components being identified by similar reference numerals sharing the same last two digits. Embodiments of the second distal assemblies 118 suitable for use with the portions 112 of FIGS. 2 and 11 are illustrated in FIGS. 2B and 11C, respectively.

In accordance with a feature of the invention, the second distal assembly 118 may be movable longitudinally relative to the second distal assembly 118. That is, the second distal assembly 118 may be afforded telescopic movement relative to the first distal assembly 18. In that regard, the catheter advantageously allows adjustability in a separation distance between the assemblies 18 and 118 and therefore the separation distance between the spines 14 and 114. Where the spines of each distal assembly are arranged such that their distal ends trace a helical pattern (e.g., about 360 degrees), the separation distance between the two assemblies can be adjusted such that the first and second helical pattern are combined or otherwise joined to form a continuous helical pattern (e.g., greater than 360 degrees, preferably greater than 540 degrees, and more preferably, about 720 degrees). In the illustrated embodiment of FIG. 15, the distal ends of the spines 14 of the first distal assembly 18 trace the generally helical pattern from about 0 degrees to about 360 degrees and the distal ends of the spines 114 of the second distal assembly 118 trace the generally helical pattern from about 360 degrees to about 720 degrees. A distance D spanned by helical pattern as defined by the proximal-most distal end of a spine 14 in the first distal assembly 18 and the distal-most distal end of a spine 114 in the second assembly 118 is adjustable by means of the telescopic movement between the first and second distal assemblies.

Figure 16:
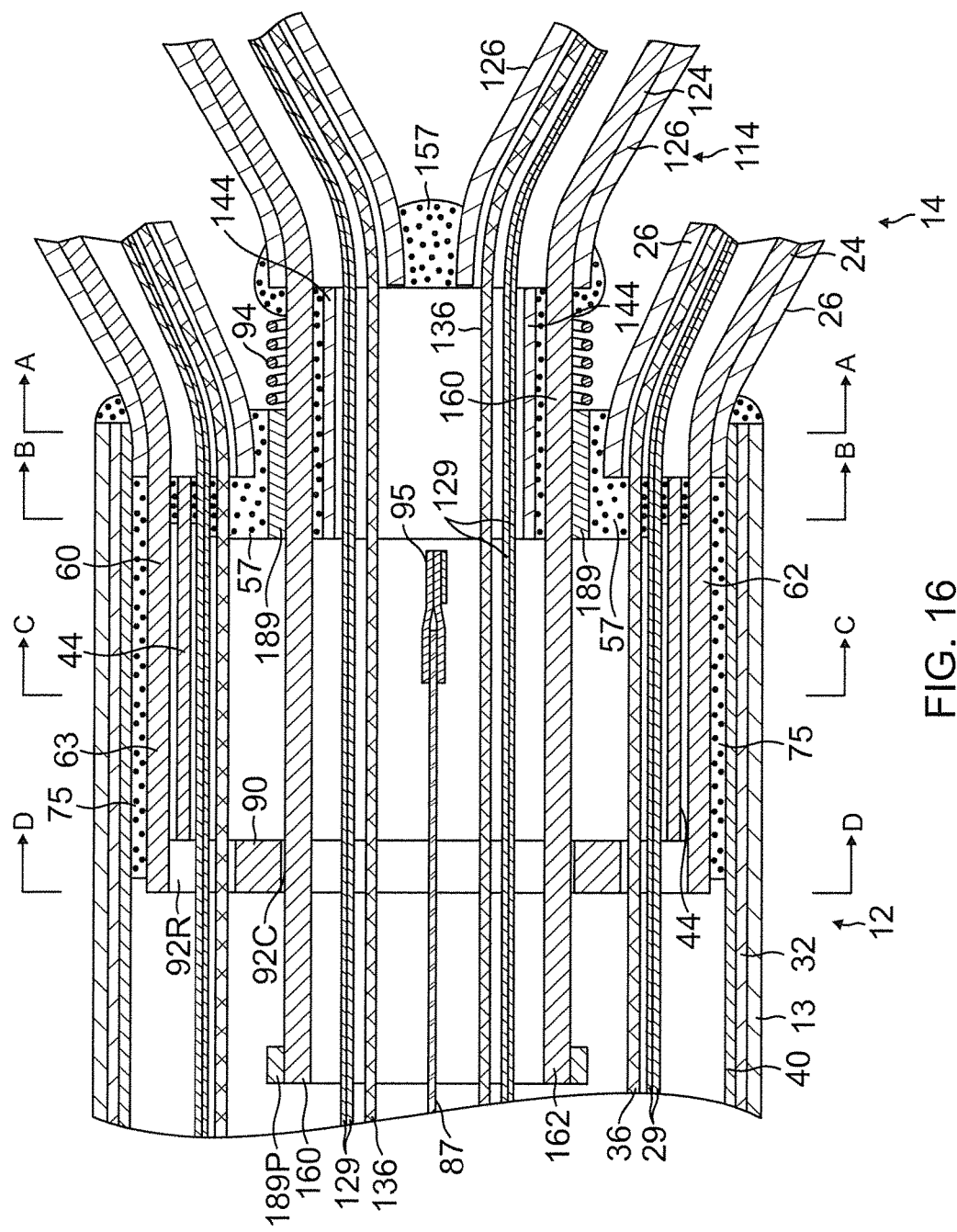
FIG. 16 is a side cross-sectional view of a junction between a first distal assembly and a proximal end of a telescopic second distal assembly, in accordance with an embodiment of the present invention.
Figure 16A:
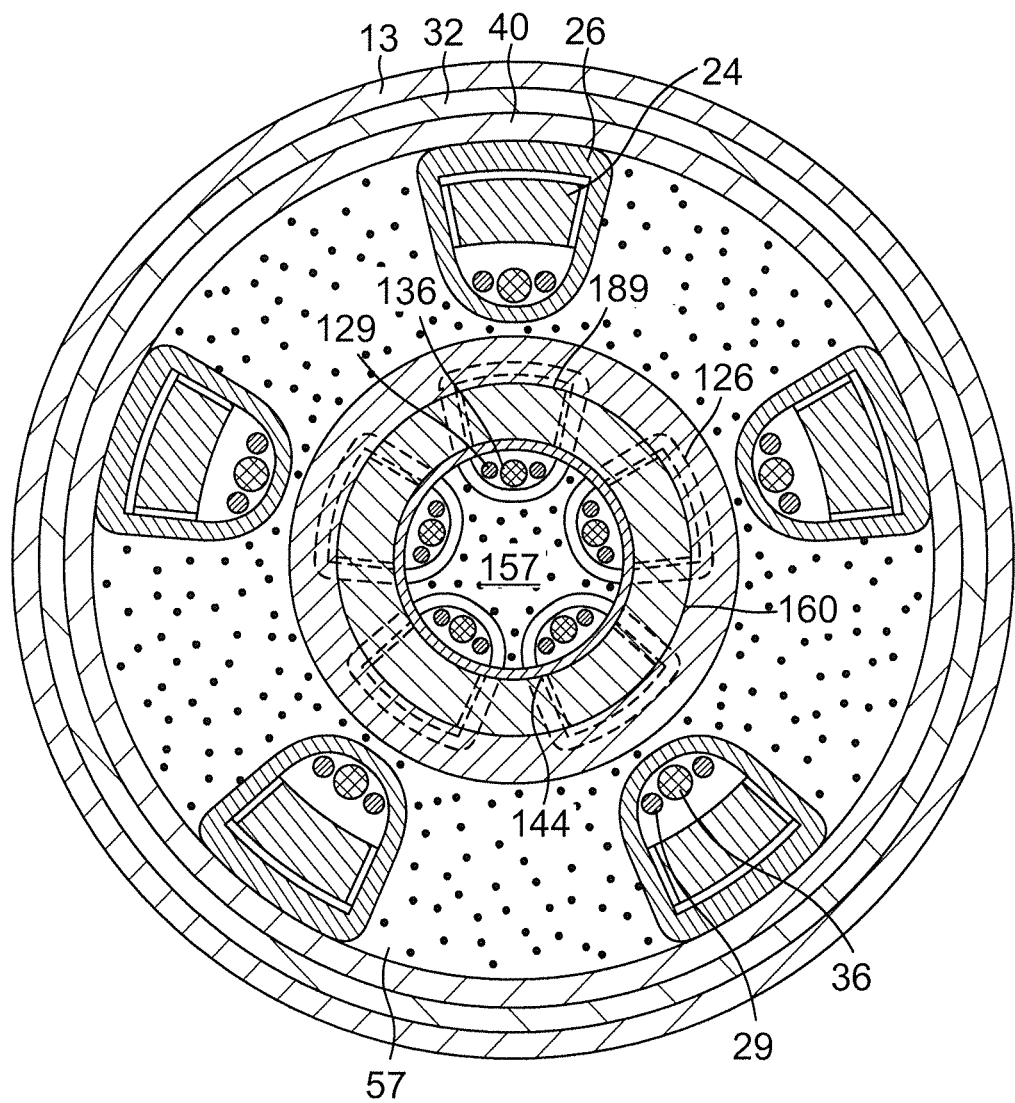
FIG. 16A is an end cross-sectional view of the junction of FIG. 16, taken along line A-A.
Figure 16B:
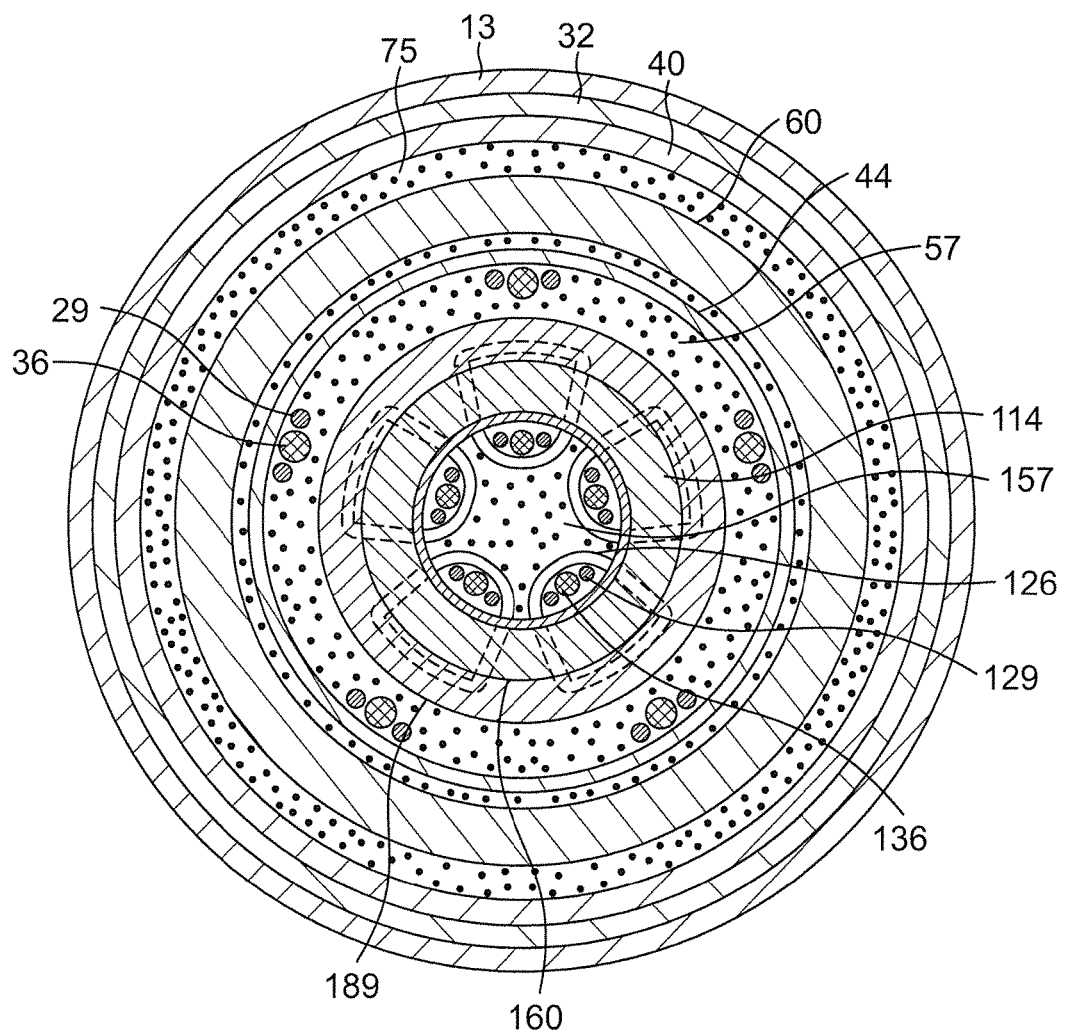
FIG. 16B is an end cross-sectional view of the junction of FIG. 16, taken along line B-B.
Figure 16C:
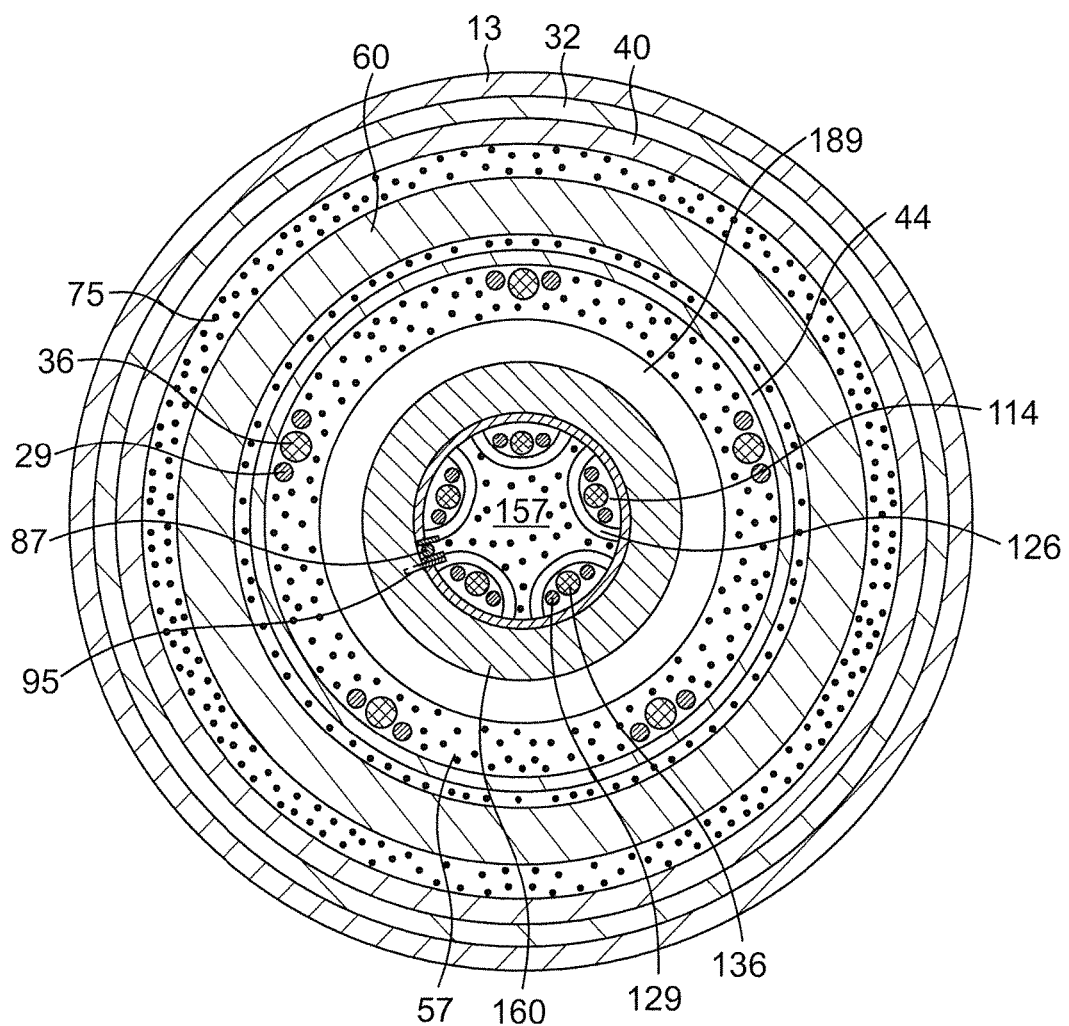
FIG. 16C is an end cross-sectional view of the junction of FIG. 16, taken along line C-C.
Figure 16D:
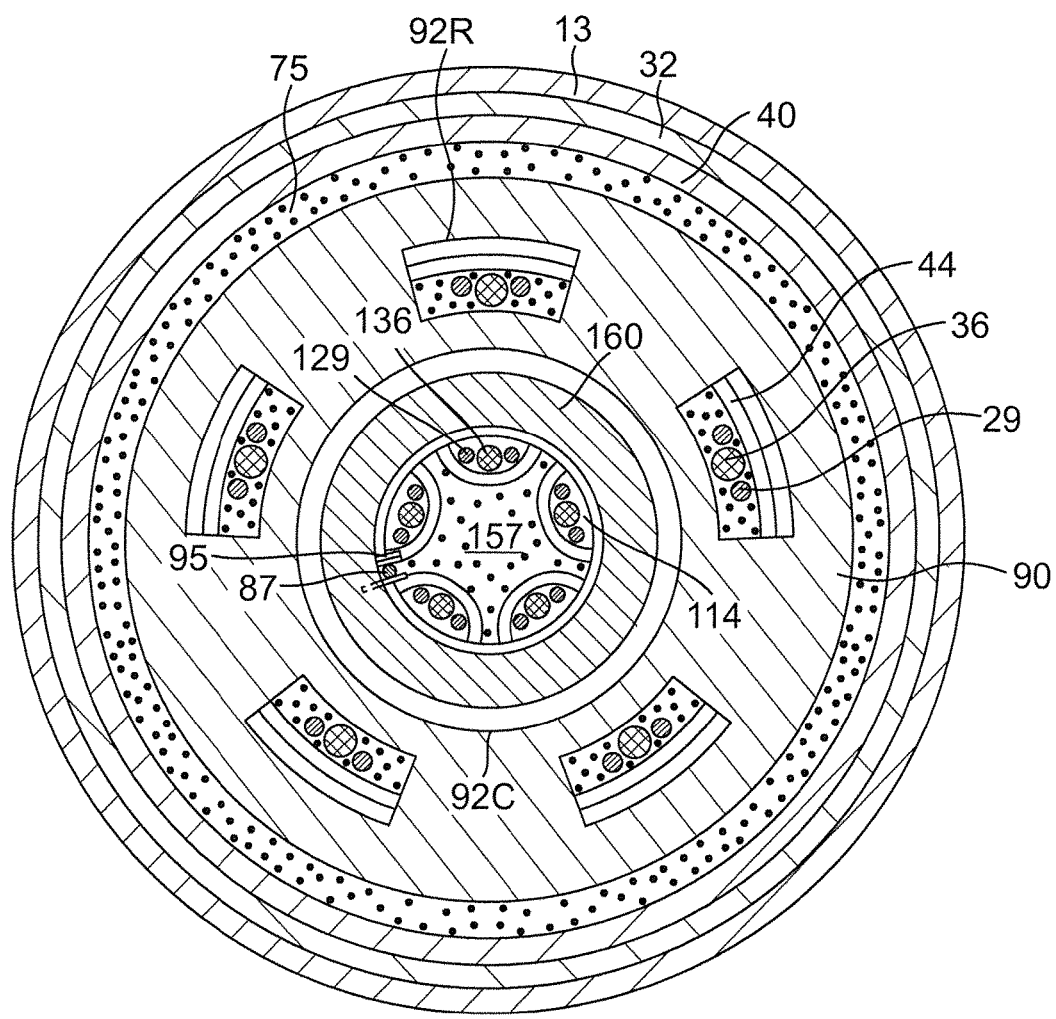
FIG. 16D is an end cross-sectional view of the junction of FIG. 16, taken along line D-D.

An embodiment of a catheter with a first distal assembly 18 and a telescopic second distal assembly 118 is illustrated in FIG. 16. Each distal assembly 18 and 118 includes a respective unibody support member 60 and 160. The first unibody support member 60 has a proximal end plate 90 with a through hole 92C that receives and translatably supports a proximal end of the unibody support member 160. A proximal annular stop 189P member is provided on at the proximal end of cylindrical body 181 to prevent the body from dislodging from the end plate 90. A distal annular stop member 189D is provided near the distal end of the body 181 to slidably support the distal end of the body 181 and limit its proximal movement relative to the unibody support member 60 of the first distal assembly 18.

The spines 114 of the distal assembly 118 are distal of the spines 14 of the distal assembly 18 and their separation distance is adjustable by means of the puller wire 87 whose distal end is anchored in a side wall of the body 181 by a T-bar 95.

It is understood that the present invention includes a catheter having two or more distal assemblies, including two or more fixed distal assemblies, or two or more telescopic distal assemblies, in axial alignment along the longitudinal axis of the catheter body 12.

Figure 17:
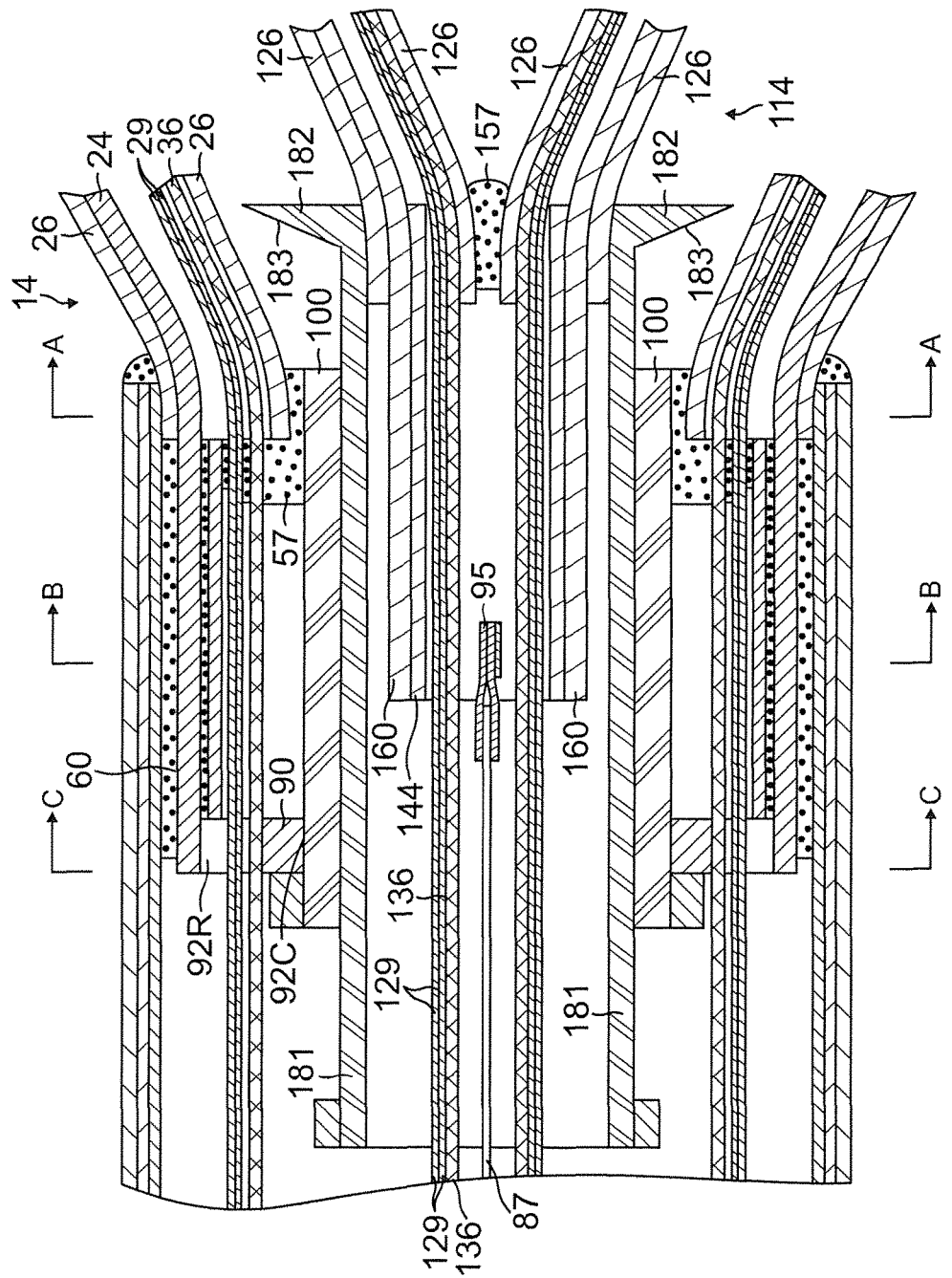
FIG. 17 is a side cross-sectional view of a junction between a first distal assembly and a proximal end of a telescopic second distal assembly, in accordance with another embodiment of the present invention.
Figure 17A:
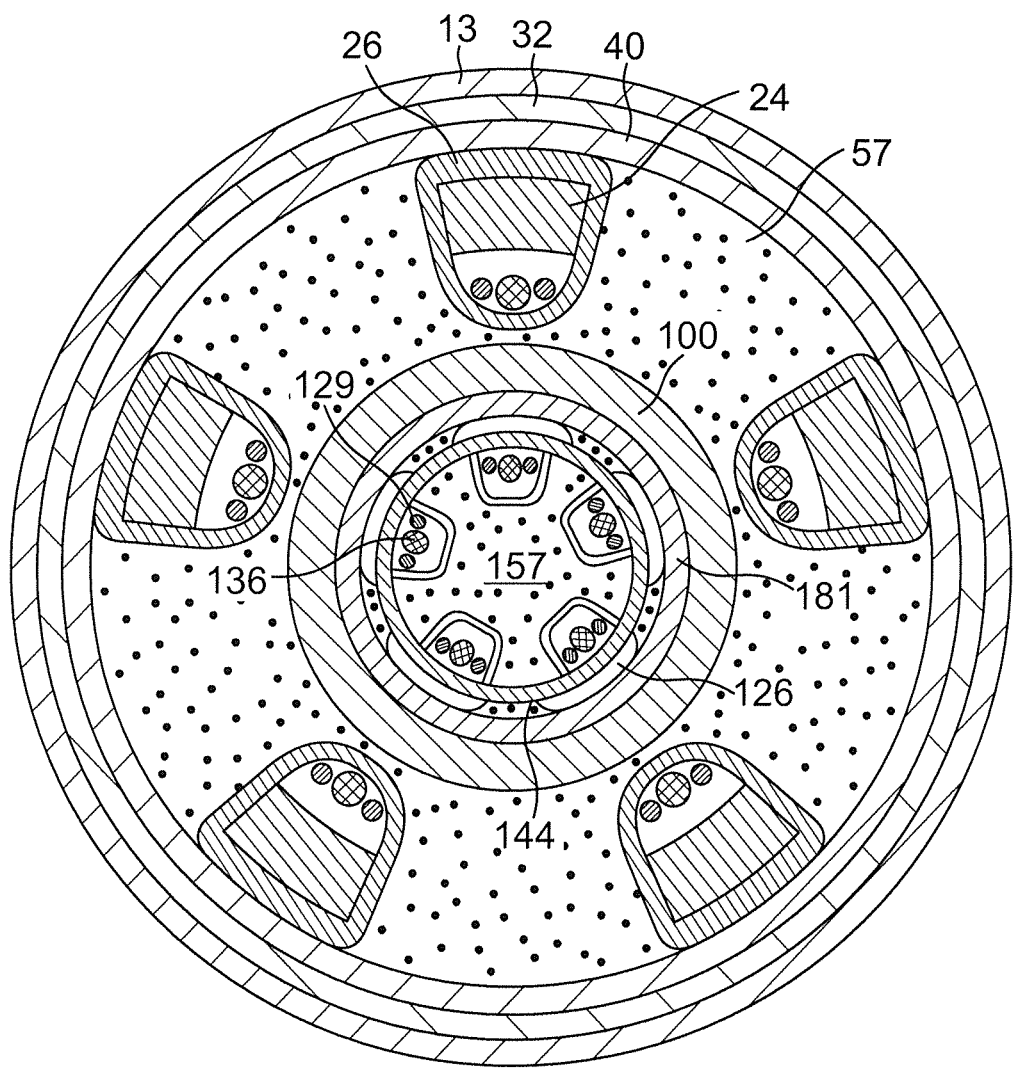
FIG. 17A is an end cross-sectional view of the junction of FIG. 17, taken along line A-A.
Figure 17B:
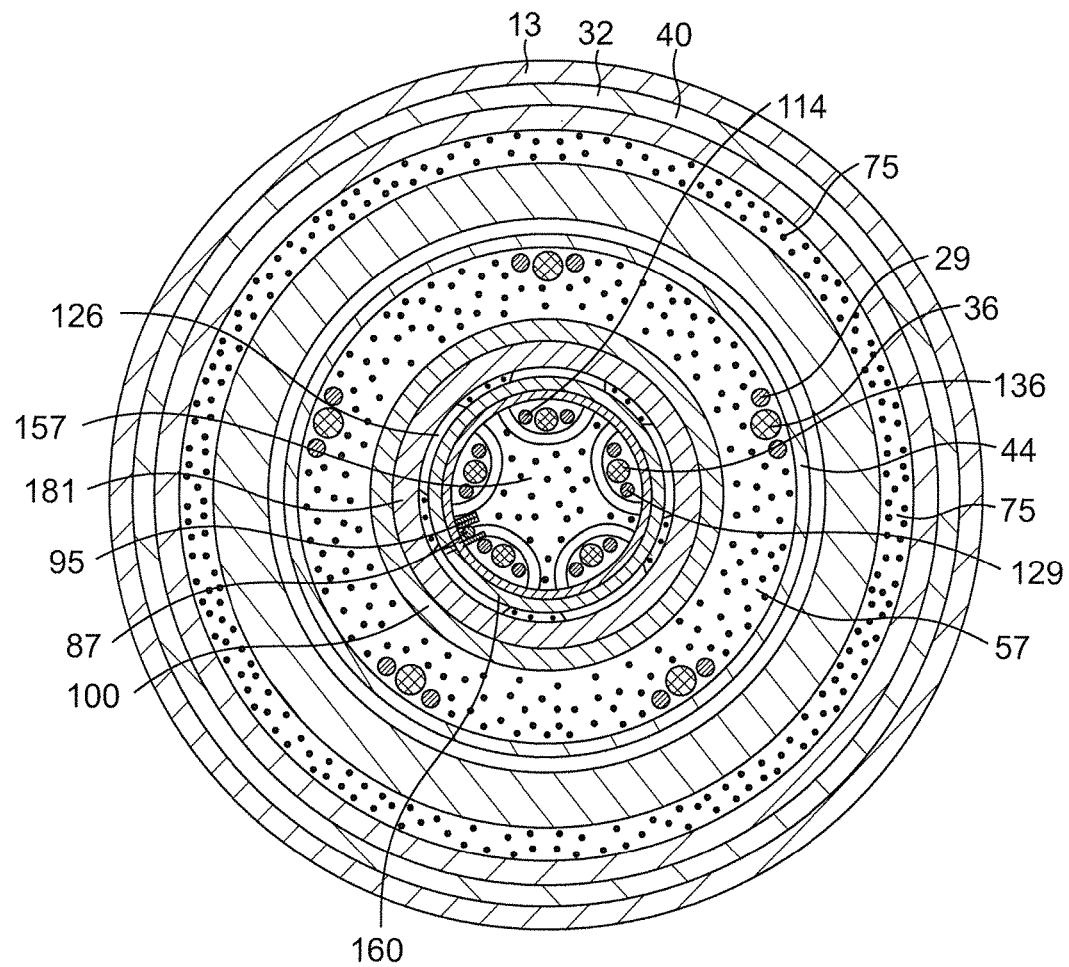
FIG. 17B is an end cross-sectional view of the junction of FIG. 17, taken along line B-B.
Figure 17C:
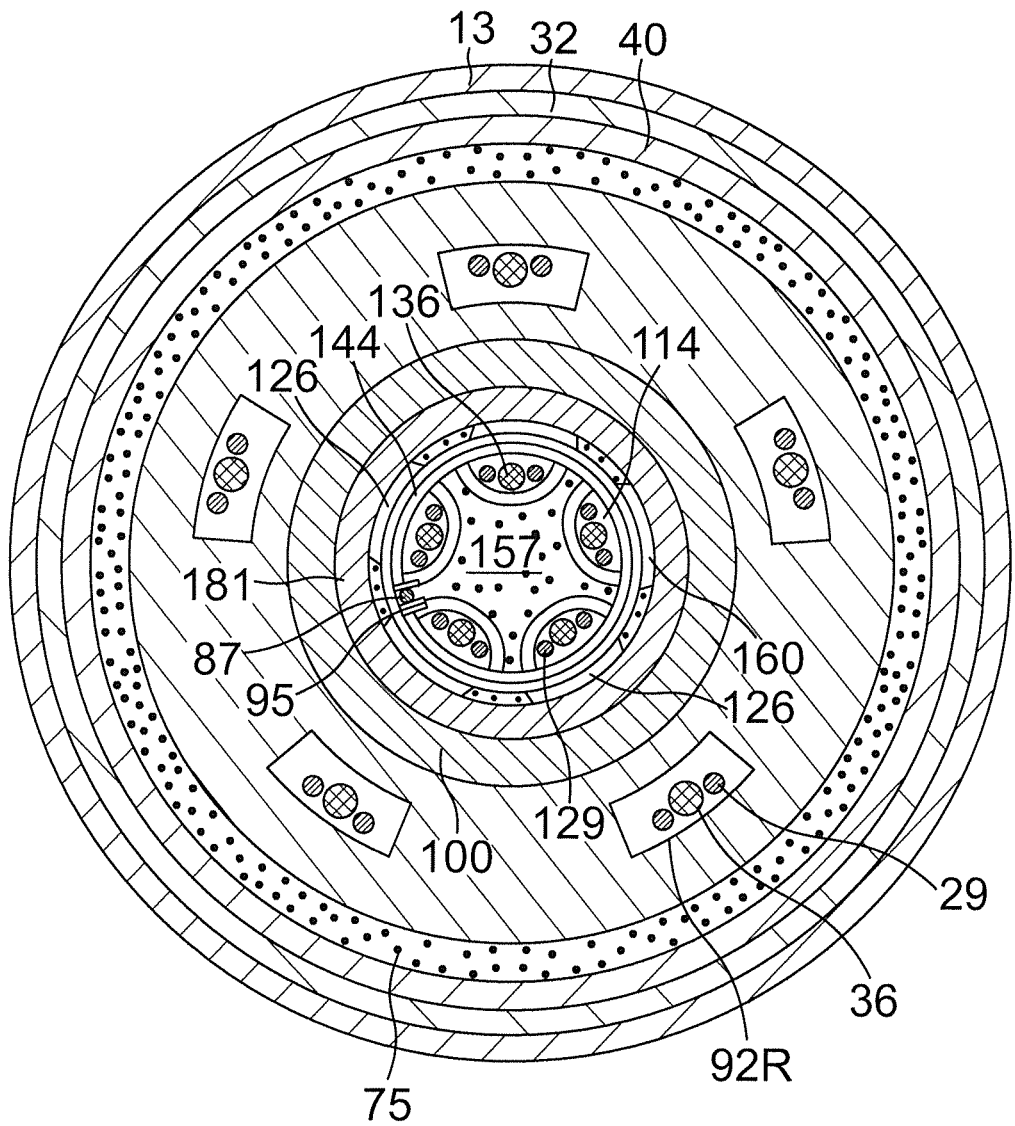
FIG. 17C is an end cross-sectional view of the junction of FIG. 17, taken along line C-C.

In another embodiment of the present invention, translational movement of the second distal assembly 118 relative to the first distal assembly 18 acts on and alters the arrangement of the spines 14 of the first distal assembly 18. For example, translational movement of the second distal assembly 118 alters the deflection or curvature of the spines 14 of the first distal assembly 18. As illustrated in FIG. 17, a unibody plunger (including components 181 and 182) of the second distal assembly 118 supports proximal ends of spines 114. The plunger has a proximal cylindrical body 181 and an enlarged distal plunger head 182 integral with an angled cam surface 183 integral with the body 181. When the plunger is drawn proximally, the cam surface 183 comes into contact with and acts on the spines 14 to spread them radially from the collapsed arrangement into the expanded arrangement. A support tube 100 fixed to the distal end of the catheter body 12 by sealing plug 57 translatably supports the body 181 for longitudinal movement relative to the distal end of the catheter body 12 in response to user manipulation of the puller wire 87. A proximal end of the tube 100 is received in slot 92C and supported by end plate 90 at the proximal end of the unibody support member 60.

To use the catheter 10 of the invention, a cardiologist or electrophysiologist introduces a guiding sheath and a dilator into the patient, as is generally known in the art, so that the distal ends of the sheath and dilator are in the region of the heart or cardiovascular structure to be mapped. In some instances, such as when it is desired to insert the catheter 10 into the left ventricle through the aortic valve in a direction opposite the blood flow, it is preferable to use a pigtail-shaped dilator 54 having a distal end 56 that forms a loop 58, as shown in FIG. 18. Specifically, the side of the loop 58 is pushed against the flaps of the valve and serves essentially as a blunt instrument to push the flaps inward so that they are temporarily inverted while the dilator and guiding sheath are advanced through the valve. By using the surface of the loop 58 to push the flaps of the valve, potential puncturing of the flaps of the valve can be avoided. In contrast, pushing the flaps with a dilator having a straight distal end can potentially puncture or otherwise damage the flaps. After the dilator and guiding sheath having been advanced through the valve with the loop 58 inside the left ventricle, the flaps of the aortic valve return to their original, natural position.

Thereafter, the dilator is removed from the guiding sheath, and the catheter 10 is introduced into the patient through the guiding sheath. To insert the catheter into the guiding sheath, the one or more distal assemblies 18, 118 must be in its collapsed arrangement, wherein each spine 14, 114 is disposed generally along the longitudinal axis of the catheter body 12. A suitable guiding sheath for use in connection with the catheter is the PREFACE™ Braided Guiding Sheath (commercially available from Biosense Webster, Inc., Diamond Bar, Calif.). Such a guiding sheath has sufficient strength to hold each support arm 24, 124 in the collapsed arrangement, such that the spines 14, 114 and also the entire remainder of the catheter can travel within the guiding sheath, from an insertion point in the patient, through a vein or artery and to a desired location in the heart. Once the distal end of the catheter has reached the desired location, such as a position within the left ventricle of the heart, relative longitudinal movement between the catheter and the guiding sheath is provided to allow at least a portion of each spine 14, 114 to protrude from the guiding sheath. Preferably the guiding sheath is moved proximally relative to the distal end of the catheter to expose the spines 114 first followed by the spines 14. When a portion of each spine 14, 114 protrudes from the guiding sheath and a compression force is no longer applied by the guiding sheath on the spines, the shape memory of the support arms 24, 124 allows the support arms to revert to a first expanded arrangement. In the first expanded arrangement, at least one electrode from each spine 14, 114 can be placed into contact with a plurality of the heart tissue. In particular, the distal ends of the spines of each distal assembly can trace a helical pattern, one more distal than the other. Where the user can adjust the separation distance between the two distal assemblies 18 and 118, the user controls the puller wire 87 to position the two assemblies such that the distal ends of the spines 14 and 114 trace a continuous helical pattern having a desired rotation, for example, greater than 360 degrees, preferably about 540 degrees, or more preferably about 720 degrees. Whether with one or more distal assemblies, the inventive catheter 10 allows the cardiologist to map and/or ablate the heart or cardiovascular structure more quickly than traditional catheters by simultaneously providing multiple contact with tissue while minimizing the risk of stenosis.

If desired, the catheter may include a steering mechanism for deflection of the distal end of the catheter body 12. With such a design, the distal end of the catheter body 12 preferably comprises a short length of tubing, e.g., 2 to 4 inches in length, that is more flexible than the remainder of the catheter body 12. A suitable steering mechanism comprises a puller wire (not shown) that extends from a proximal end in the control handle 16, through the central lumen 15 in the catheter body 12 and into an off axis lumen in the short length of tubing. Within the catheter body 12, the puller wire extends through a closely wound coil that is bendable but substantially non-compressible. The coil is fixed near the proximal and distal ends of the catheter body 12 and prevents deflection of the catheter body 12. The distal end of the puller wire is anchored at the distal end of the short length of tubing in the off axis lumen. The proximal end of the puller wire is anchored to a movable member in the handle 16 that can be moved relative to the catheter body 12. Proximal movement of the movable member relative to the catheter body 12 results in deflection of the short length of tubing. An example of such a steering mechanism and construction is described in more detail in U.S. Pat. No. 6,064,905, the disclosure of which is incorporated herein by reference. When incorporating a steering mechanism into the inventive catheter 10, it may be desirable to include a location sensor at the distal end of the catheter body 12. As would be recognized by one skilled in the art, of a steering mechanism is not including, the handle 16 can be eliminated, although it is described to maintain the handle for ease of use by the cardiologist.

What is claimed is:

1. A catheter, comprising:
   an elongated catheter body; and
   a distal assembly distal of the elongated catheter body and comprising at least four spines, each of the at least four spines having a proximal end fixedly attached to a distal end of the elongated catheter body and a free distal end,
   wherein each of the at least four spines comprises:
   a support arm having shape memory;
   a non-conductive covering in surrounding relation to the support arm; and
   at least one electrode;
   wherein the at least four spines are arranged in a radial pattern about a longitudinal axis of the distal assembly and a length of each of the at least four spines increases in radial progression about the longitudinal axis, and when the distal assembly is in an expanded arrangement, each of the at least four spines extends radially outward from the catheter body.

2. The catheter of claim 1, wherein the at least one electrode of each of the at least four spines is mounted at or near the free distal end of a corresponding one of the at least four spines and is electrically isolated from the support arm.

3. The catheter of claim 1, wherein the at least one electrode includes at least one ring electrode mounted in surrounding relation to the non-conductive covering.

4. The catheter of claim 1, wherein each support arm comprises nitinol.

5. The catheter of claim 1, wherein when the distal assembly is in a collapsed arrangement, each of the at least four spines is disposed generally along the longitudinal axis of the elongated catheter body.

6. The catheter of claim 1, wherein when the distal assembly is in its expanded arrangement, each of the at least four spines extends radially outwardly from the elongated catheter body and forms a curved shape.

7. The catheter of claim 1, further comprising a plunger having a cam surface to deflect the at least four spines.

* * * * *